US010168445B2

(12) United States Patent
Morton

(10) Patent No.: US 10,168,445 B2
(45) Date of Patent: Jan. 1, 2019

(54) HAND-HELD PORTABLE BACKSCATTER INSPECTION SYSTEM

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 214 days.

(21) Appl. No.: 15/074,787

(22) Filed: Mar. 18, 2016

(65) Prior Publication Data
US 2017/0023696 A1 Jan. 26, 2017

Related U.S. Application Data

(60) Provisional application No. 62/136,362, filed on Mar. 20, 2015, provisional application No. 62/136,322, filed on Mar. 20, 2015, provisional application No. 62/136,315, filed on Mar. 20, 2015, provisional application No. 62/136,305, filed on Mar. 20, 2015, provisional application No. 62/136,299, filed on Mar. 20, 2015.

(51) Int. Cl.
*G01N 23/04* (2018.01)
*G01V 5/00* (2006.01)
*G01N 23/203* (2006.01)

(52) U.S. Cl.
CPC ......... *G01V 5/0025* (2013.01); *G01N 23/203* (2013.01); *G01V 5/0066* (2013.01)

(58) Field of Classification Search
CPC ...... G01V 5/00; G01V 5/0025; G01V 5/0066; G01V 5/0008; G01V 5/0016; G01N 23/20; G01N 23/203; G01N 23/20008; G01N 23/04; G21K 1/06
USPC .................................... 378/70, 86, 87, 88
See application file for complete search history.

(56) References Cited

U.S. PATENT DOCUMENTS

| 4,045,672 A | 8/1977 | Watanabe |
| 4,242,583 A | 12/1980 | Annis |
| 5,056,129 A | 10/1991 | Steinmeyer |
| 5,665,969 A | 9/1997 | Beusch |

(Continued)

FOREIGN PATENT DOCUMENTS

WO 2018064434 4/2018

OTHER PUBLICATIONS

International Search Report for PCT/US2016/023240, dated Jul. 12, 2016.

(Continued)

*Primary Examiner* — Jurie Yun
(74) *Attorney, Agent, or Firm* — Novel IP

(57) ABSTRACT

The present specification describes a compact, hand-held probe or device that uses the principle of X-ray backscatter to provide immediate feedback to an operator about the presence of scattering and absorbing materials, items or objects behind concealing barriers irradiated by ionizing radiation, such as X-rays. Feedback is provided in the form of a changing audible tone whereby the pitch or frequency of the tone varies depending on the type of scattering material, item or object. Additionally or alternatively, the operator obtains a visual scan image on a screen by scanning the beam around a suspect area or anomaly.

19 Claims, 17 Drawing Sheets

(56) References Cited

U.S. PATENT DOCUMENTS

| | | |
|---|---|---|
| 6,081,580 A | 6/2000 | Grodzins |
| 6,151,381 A | 11/2000 | Grodzins |
| 6,192,104 B1 | 2/2001 | Adams |
| 6,249,567 B1 | 6/2001 | Rothschild |
| 6,282,260 B1 | 8/2001 | Grodzins |
| 6,320,933 B1 | 11/2001 | Grodzins |
| 6,424,695 B1 | 7/2002 | Grodzins |
| 6,442,233 B1 | 8/2002 | Grodzins |
| 6,453,007 B2 | 9/2002 | Adams |
| 6,459,761 B1 | 10/2002 | Grodzins |
| 6,459,764 B1 | 10/2002 | Chalmers |
| 6,542,574 B2 | 4/2003 | Grodzins |
| 6,546,072 B1 | 4/2003 | Chalmers |
| 6,621,888 B2 | 9/2003 | Grodzins |
| 6,658,087 B2 | 12/2003 | Chalmers |
| 6,965,662 B2 | 11/2005 | Eppler |
| 7,099,434 B2 | 8/2006 | Adams |
| 7,218,704 B1 | 5/2007 | Adams |
| 7,366,282 B2 | 4/2008 | Peschmann |
| 7,400,701 B1 | 7/2008 | Cason |
| 7,417,440 B2 | 8/2008 | Peschmann |
| 7,505,556 B2 | 3/2009 | Chalmers |
| 7,505,562 B2 | 3/2009 | Dinca |
| 7,551,715 B2 | 6/2009 | Rothschild |
| 7,551,718 B2 | 6/2009 | Rothschild |
| 7,555,099 B2 | 6/2009 | Rothschild |
| 7,579,845 B2 | 8/2009 | Peschmann |
| 7,593,506 B2 | 9/2009 | Cason |
| 7,783,005 B2 | 8/2010 | Kaval |
| 7,856,081 B2 | 12/2010 | Peschmann |
| 7,924,979 B2 | 4/2011 | Rothschild |
| 7,995,707 B2 | 8/2011 | Rothschild |
| 8,054,938 B2 | 11/2011 | Kaval |
| 8,138,770 B2 | 3/2012 | Peschmann |
| 8,194,822 B2 | 6/2012 | Rothschild |
| 8,275,091 B2 | 9/2012 | Morton |
| 8,275,092 B1 | 9/2012 | Zhang |
| 8,325,871 B2 | 12/2012 | Grodzins |
| 8,345,819 B2 | 1/2013 | Mastronardi |
| 8,389,942 B2 | 3/2013 | Morton |
| 8,428,217 B2 | 4/2013 | Peschmann |
| 8,433,036 B2 | 4/2013 | Morton |
| 8,442,186 B2 | 5/2013 | Rothschild |
| 8,503,605 B2 | 8/2013 | Morton |
| 8,582,720 B2 | 11/2013 | Morton |
| 8,668,386 B2 | 3/2014 | Morton |
| 8,731,137 B2 | 5/2014 | Arroyo |
| 8,735,833 B2 | 5/2014 | Morto |
| 8,750,452 B2 | 6/2014 | Kaval |
| 8,750,454 B2 | 6/2014 | Gozani |
| 8,774,357 B2 | 7/2014 | Morton |
| 8,824,632 B2 | 9/2014 | Mastronardi |
| 8,831,176 B2 | 9/2014 | Morto |
| 8,842,808 B2 | 9/2014 | Rothschild |
| 8,903,045 B2 | 12/2014 | Schubert |
| 8,903,046 B2 | 12/2014 | Morton |
| 8,908,831 B2 | 12/2014 | Bendahan |
| 8,929,509 B2 | 1/2015 | Morton |
| 8,993,970 B2 | 3/2015 | Morton |
| 9,042,511 B2 | 5/2015 | Peschmann |
| 9,052,403 B2 | 6/2015 | Morton |
| 9,057,679 B2 | 6/2015 | Morton |
| 9,069,101 B2 | 6/2015 | Arroyo, Jr. |
| 9,121,958 B2 | 9/2015 | Morton |
| 9,128,198 B2 | 9/2015 | Morton |
| 9,146,201 B2 | 9/2015 | Schubert |
| 9,207,195 B2 | 12/2015 | Gozani |
| 9,223,050 B2 | 12/2015 | Kaval |
| 9,268,058 B2 | 2/2016 | Peschmann |
| 9,285,488 B2 | 3/2016 | Arodzero |
| 9,417,060 B1 | 8/2016 | Schubert |
| 9,465,135 B2 | 10/2016 | Morton |
| 9,535,019 B1 | 1/2017 | Rothschild |
| 9,562,866 B2 | 2/2017 | Morton |
| 9,632,205 B2 | 4/2017 | Morton |
| 9,658,343 B2 | 5/2017 | Arodzero |
| 9,791,590 B2 | 10/2017 | Morton |
| 9,823,201 B2 | 11/2017 | Morton |
| 9,841,386 B2 | 12/2017 | Grodzins |
| 2003/0223549 A1 | 12/2003 | Winsor |
| 2004/0004482 A1 | 1/2004 | Bouabdo |
| 2005/0053199 A1 | 3/2005 | Miles |
| 2005/0135560 A1 | 6/2005 | Dafni |
| 2007/0019781 A1 | 1/2007 | Haras |
| 2008/0219804 A1 | 9/2008 | Chattey |
| 2008/0273652 A1 | 11/2008 | Arnold |
| 2009/0309034 A1 | 12/2009 | Yoshida |
| 2012/0199753 A1 | 8/2012 | Chuang |
| 2013/0195248 A1* | 8/2013 | Rothschild ........... G01N 23/203 378/86 |
| 2013/0315368 A1 | 11/2013 | Turner |
| 2014/0105367 A1 | 4/2014 | Horvarth |
| 2015/0055751 A1 | 2/2015 | Funk |
| 2015/0060673 A1* | 3/2015 | Zimdars ................ G01S 17/88 250/341.2 |
| 2015/0168589 A1 | 6/2015 | Morton |
| 2016/0025888 A1 | 1/2016 | Peschmann |
| 2016/0025889 A1 | 1/2016 | Morton |
| 2016/0170077 A1 | 6/2016 | Morton |
| 2016/0223706 A1 | 8/2016 | Franco |
| 2017/0059739 A1 | 3/2017 | Mastronardi |
| 2017/0184516 A1* | 6/2017 | Chen ....................... G01T 7/00 |
| 2017/0299526 A1 | 10/2017 | Morton |
| 2017/0299764 A1 | 10/2017 | Morton |
| 2017/0315242 A1 | 11/2017 | Arodzero |
| 2018/0128935 A1 | 5/2018 | Morton |

OTHER PUBLICATIONS

International Search Report for PCT/US17/54211, dated Jan. 18, 2018.

\* cited by examiner

HAND-HELD PORTABLE BACKSCATTER INSPECTION SYSTEM

CROSS-REFERENCE

The present application relies on U.S. Patent Provisional Application No. 62/136,299, entitled "Handheld Portable Backscatter Inspection System" and filed on Mar. 20, 2015, for priority.

The present application also relies on U.S. Patent Provisional Application No. 62/136,305, entitled "Handheld Portable Backscatter Inspection System" and filed on Mar. 20, 2015, for priority.

The present application also relies on U.S. Patent Provisional Application No. 62/136,315, entitled "Handheld Portable Backscatter Inspection System" and filed on Mar. 20, 2015, for priority.

The present application also relies on U.S. Patent Provisional Application No. 62/136,322, entitled "Handheld Portable Backscatter Inspection System" and filed on Mar. 20, 2015, for priority.

The present application also relies on U.S. Patent Provisional Application No. 62/136,362, entitled "Handheld Portable Backscatter Inspection System" and filed on Mar. 20, 2015, for priority.

All of the above-mentioned applications are herein incorporated by reference in their entirety.

FIELD

The present specification generally relates to a portable backscatter scanning system, and in particular, relates to a system which can be carried by an operator by hand to sites of inspection, including confined locations, and subsequently used to scan for detection of concealed materials and objects.

BACKGROUND

Materials, such as narcotics, explosives or currency, and objects, such as weapons or people, are concealed within or behind barriers with the intention that the materials or objects remain undetected by routine or targeted security checks.

Today, scanning devices are well known which use a variety of sensing methods to detect concealed materials and objects. These scanning devices include transmission X-ray imaging systems, Compton scatter-based backscatter imaging systems, chemical sniffing trace detection equipment, thermal imaging camera systems and so on. Such scanning devices may be used alone or in combination to provide a comprehensive level of security. However, such devices tend either to be large and expensive (e.g. transmission X-ray imaging systems) or insensitive to carefully hidden materials (e.g. trace detection equipment and camera systems) which means that their utility is restricted to certain high throughput situations such as sea ports and land borders, airport checkpoints and so on.

Therefore, what is needed is a compact, light-weight, portable and hand-held system or device that can be maneuvered to reach relatively inaccessible locations and scan behind concealing barriers that are otherwise opaque against chemical and optical probes. Such a system or device should be able to provide immediate feedback if a suspicious material, object or anomaly is detected and should allow an operator to obtain information about the concealed material or object, for threat resolution, without the need to breach the concealing barrier.

SUMMARY

In some embodiments, the present specification discloses a method for scanning an object by projecting a shaped X-ray beam from a hand-held imaging device, where the device includes a housing enclosing an X-ray tube that emits the shaped X-ray beam, a plurality of detectors for generating scan data corresponding to a plurality of detected X-ray beams scattered from the object, a processor in communication with a gyroscope and an accelerometer, and an acquisition system in communication with a speaker, a display, the processor and the plurality of detectors. In some embodiments, the method includes using the processor for calculating a plurality of active pixels corresponding to a location of interaction of the shaped X-ray beam on the object; using the processor for calculating a time duration, at each of said plurality of active pixels, for which the shaped X-ray beam is present over each of said plurality of active pixels; and using the processor to generate an image, on said display, of the object after correcting the scan data, at each of said plurality of active pixels, using said time duration.

In some embodiments, the shaped X-ray beam is a pencil beam.

In some embodiments, the shaped X-ray beam is a cone beam.

In some embodiments, the shaped X-ray beam is a fan beam.

In some embodiments, the shaped X-ray beam is a single-axis rotating beam.

In some embodiments, the shaped X-ray beam is a dual-axis rotating beam.

In some embodiments, the hand-held imaging device is swept to scan the object using a coarse scanning pattern to identify at least one anomaly, with reference to the object, prior to calculating said plurality of active pixels, calculating said time duration and generating said image. Optionally, the anomaly is identified based on a change in audible tone generated by the speaker. Optionally, the processor and speaker are adapted to generate said audible tone such that a pitch or frequency of said audible tone varies in proportion to said scan data.

Optionally, upon identification of said at least one anomaly, the hand-held imaging device is swept to scan the object using a fine scanning pattern for calculating said plurality of active pixels, calculating said time duration and generating said image.

In some embodiments, the processor receives second data which is generated by the accelerometer and is indicative of a movement of the shaped X-ray beam being projected on the object. In some embodiments, the method includes based on said second data: using the processor for calculating a plurality of active pixels corresponding to a new location of interaction of the shaped X-ray beam on the object; using the processor for calculating a time duration, at each of said plurality of active pixels, for which the shaped X-ray beam is present over each of said plurality of active pixels; and using the processor for generating an updated image, on said display, of the object after correcting the scan data, at each of said plurality of active pixels, using said time duration.

In some embodiments, the new location is associated with an updated first data generated by the gyroscope, and wherein said updated first data is indicative of a new direction of the shaped X-ray beam being projected on the object.

In some embodiments, the acquisition system sums said detected scan data over a sampling duration ranging between 0.01 ms and 100 ms.

In some embodiments, the acquisition system sums said detected scan data over a sampling duration of 1 ms.

In some embodiments, a voltage of the X-ray tube ranges between 30 kV and 100 kV.

In some embodiments, a current of the X-ray tube ranges between 0.1 mA and 5 mA.

In some embodiments, the location is associated with a first data generated by the gyroscope, and wherein said first data is indicative of a direction of the shaped X-ray beam being projected on the object.

In some embodiments, the present specification discloses a system for a hand-held imaging device for scanning an object by projecting a shaped X-ray beam. In some embodiments, the system includes a housing having a central longitudinal axis and including: a plurality of detectors for generating scan data corresponding to a plurality of detected X-ray beams scattered from the object; a gyroscope; an accelerometer; an acquisition system in communication with a display and said plurality of detectors; and a processor in communication with said gyroscope, said accelerometer and said acquisition system. In some embodiments, said processor is configured for: calculating a plurality of active pixels corresponding to a location of interaction of the shaped X-ray beam on the object; calculating a time duration, at each of said plurality of active pixels, for which the shaped X-ray beam is present over each of said plurality of active pixels; and generating an image, on said display, of the object after correcting the scan data, at each of said plurality of active pixels, using said time duration.

In some embodiments, the shaped X-ray beam is a pencil beam.

In some embodiments, the shaped X-ray beam is a cone beam.

In some embodiments, the shaped X-ray beam is a fan beam.

In some embodiments, the shaped X-ray beam is a single-axis rotating beam.

In some embodiments, the shaped X-ray beam is a dual-axis rotating beam.

In some embodiments, the housing has an upper surface, a base opposite and parallel to said upper surface, a front surface, a rear surface opposite and parallel to said front surface, a first side and a second side opposite and parallel to said first side, and wherein said upper surface has at least one handle. Optionally, the housing is configured as a first cuboid, bearing said front surface, which tapers along the central longitudinal axis into a trapezoidal prism culminating in said rear surface.

Optionally, the shaped X-ray beam emerges through an opening at a center of said front surface in a direction substantially perpendicular to said front surface. Optionally, the plurality of detectors are positioned adjacent to and behind said front surface surrounding said opening at the center of said front surface.

In some embodiments, the system includes a speaker, wherein said processor and speaker are adapted to generate an audible tone such that a pitch or frequency of said audible tone varies in proportion to said scan data.

Optionally, the housing further comprises a plurality of vanes for collimating a plurality of X-ray beams scattered from the object. Optionally, said plurality of vanes are arranged in planes that are substantially parallel to each other. Optionally, said plurality of vanes are arranged in planes that are substantially parallel to each other and in a direction substantially perpendicular to an orientation of a plane of a fan beam. Optionally, said plurality of vanes is arranged in planes in a substantially diverging orientation with respect to each other. Optionally, said plurality of vanes is arranged in planes in a substantially converging orientation with respect to each other.

Optionally, the housing further comprises a grid of a plurality of collimator elements for collimating a plurality of X-ray beams scattered from the object. Still optionally, said grid comprises first and second sets of a plurality of combs, each of said plurality of combs having teeth, wherein the teeth of said first set of combs in a first direction interlock with the teeth of said second set of combs in a second direction, and wherein said second direction is substantially orthogonal to said first direction. Optionally, said teeth are arranged in planar directions substantially parallel to an orientation of said shaped X-ray beam. Still optionally, said teeth are arranged in planar directions substantially parallel to each other. Optionally, said teeth are arranged in planar orientations that are substantially divergent with respect to each other. Optionally, said teeth are arranged in planar orientations that are substantially convergent with respect to each other. Optionally, each of said plurality of detectors maps to an area on the object, wherein said area is defined by a solid angle of a cone beam and an acceptance angle of each of said plurality of collimator elements.

Optionally, the housing further comprises a first rotating collimator having a first transmission pattern and a second rotating collimator having a second transmission pattern, said first and second transmission patterns defining said shaped X-ray beam. Optionally, said first transmission pattern defines a radial position of a pencil beam while said second transmission pattern defines an azimuthal angle of said pencil beam. Optionally, said first and second collimators rotate in lock step with each other, and wherein said first collimator rotates at a first speed while said second collimator rotates at a second speed. Optionally, said second speed is greater than said first speed. Optionally, said first and second collimators are substantially circular disks having differing radii. Optionally, said first and second collimators are substantially circular disks having equal radii. Optionally, said first transmission pattern is a slit extending in a spirally curved configuration from a point proximate to a center point of said first collimator to a point proximate to a circumference of said first collimator, and wherein said second transmission pattern is a slit extending radially from a point proximate to a center of said second collimator to a point proximate to a circumference of said second collimator.

Optionally, said housing further comprises a rotating collimator having a transmission pattern defining the shaped X-ray beam, the rotating collimator supported and partially surrounded by an oscillating shaped cradle. Optionally, said collimator rotates at a speed ranging between 100 to 5000 RPM. Optionally, said collimator rotates at a speed of 2000 RPM. Optionally, said rotating collimator causes said shaped X-ray beam to sweep a trajectory in a substantially vertical plane such that a focal spot of said shaped X-ray beam is in a plane of said rotating collimator and on a central longitudinal axis of said housing, and wherein said oscillating shaped cradle causes said shaped X-ray beam to sweep left to right, repeatedly, over said substantially vertical plane. Optionally, said collimator is a substantially circular disk having a first radius while said shaped cradle is substantially semi-circular having a second radius, and wherein said second radius is greater than said first radius. Optionally, said collimator is a substantially circular disk having a radius while said shaped cradle is substantially 'U' or 'C' shaped. Optionally, said transmission pattern is an opening at a point between a center and a circumference of said collimator, and wherein said rotating and oscillating movements together cause said shaped X-ray beam to move in a raster pattern over a two dimensional area of the object.

In some embodiments, the present specification is directed toward a method of scanning an object by projecting a shaped X-ray beam from a hand-held imaging device. In some embodiments, the device includes a housing enclosing an X-ray tube that emits the shaped X-ray beam, a plurality of detectors for generating scan data corresponding to a plurality of detected X-ray beams scattered from the object, a processor in communication with a gyroscope and an accelerometer, and an acquisition system in communication with a speaker, a display, said processor and said plurality of detectors. In some embodiments, the method includes receiving first data by the processor, wherein said first data is generated by the gyroscope and is indicative of a direction of the shaped X-ray beam being projected on the object; using the processor for calculating a plurality of active pixels corresponding to a location of interaction of the shaped X-ray beam on the object, wherein said location is associated with said first data; using the processor for calculating a time duration, at each of said plurality of active pixels, for which the shaped X-ray beam is present over each of said plurality of active pixels; and using the processor for generating an image, on said display, of the object after correcting the scan data, at each of said plurality of active pixels, using said time duration.

In some embodiments, the shaped X-ray beam is in the form of a pencil beam.

In some embodiments, the hand-held imaging device is swept to scan the object using a coarse scanning pattern to identify at least one anomaly, with reference to the object, prior to receiving said first data, calculating said plurality of active pixels, calculating said time duration and generating said image. Optionally, the anomaly is identified based on a change in audible tone generated by the speaker. Still optionally, a pitch or frequency of said audible tone is proportional to said generated scan data.

Optionally, upon identification of said at least one anomaly, the hand-held imaging device is swept to scan the object using a fine scanning pattern for receiving said first data, calculating said plurality of active pixels, calculating said time duration and generating said image. Optionally, the method further includes receiving second data by the processor, wherein said second data is generated by the accelerometer and is indicative of a movement of the shaped X-ray beam being projected on the object. In some embodiments, based on said second data, the method includes receiving updated first data by the processor indicative of a new direction of the shaped X-ray beam being projected on the object; using the processor for calculating a plurality of active pixels corresponding to a location of interaction of the shaped X-ray beam on the object, wherein said location is associated with said updated first data indicative of the new direction; using the processor for calculating a time duration, at each of said plurality of active pixels, for which the shaped X-ray beam is present over each of said plurality of active pixels; and using the processor for generating an updated image, on said display, of the object after correcting the scan data, at each of said plurality of active pixels, using said time duration.

In some embodiments, the acquisition system sums said detected scan data over a sampling duration ranging between 0.01 ms and 100 ms.

In some embodiments, the acquisition system sums said detected scan data over a sampling duration of 1 ms.

In some embodiments, a voltage of the X-ray tube ranges between 30 kV and 100 kV.

In some embodiments, a current of the X-ray tube ranges between 0.1 mA and 5 mA.

In some embodiments, the present specification is directed towards a system for a hand-held imaging device for scanning an object by projecting a shaped X-ray beam, where the device includes a housing having a central longitudinal axis. In some embodiments, the housing includes a plurality of detectors for generating scan data corresponding to a plurality of detected X-ray beams scattered from the object; a gyroscope; an accelerometer; an acquisition system in communication with a speaker, a display and said plurality of detectors; and a processor in communication with said gyroscope, said accelerometer and said acquisition system. In some embodiments, said processor is configured for receiving first data generated by the gyroscope and indicative of a direction of the shaped X-ray beam being projected on the object; calculating a plurality of active pixels corresponding to a location of interaction of the shaped X-ray beam on the object, wherein said location is associated with said first data; calculating a time duration, at each of said plurality of active pixels, for which the shaped X-ray beam is present over each of said plurality of active pixels; and generating an image, on said display, of the object after correcting the scan data, at each of said plurality of active pixels, using said time duration.

In some embodiments, the shaped X-ray beam is in the form of a pencil beam.

In some embodiments, the housing has an upper surface, a base opposite and parallel to said upper surface, a front surface, a rear surface opposite and parallel to said front surface, a first side and a second side opposite and parallel to said first side, and wherein said upper surface has at least one handle. Optionally, the housing is configured as a first cuboid, bearing said front surface, which tapers along the central longitudinal axis into a second cuboid culminating in said rear surface. Optionally, the shaped X-ray beam emerges through an opening at a center of said front surface in a direction substantially perpendicular to said front surface. Optionally, the plurality of detectors are positioned adjacent to and behind said front surface surrounding said opening at the center of said front surface. Optionally, there are four sets of detectors.

In some embodiments, the present specification is directed towards a method of scanning an object by projecting a shaped X-ray beam from a hand-held imaging device. In some embodiments, the device includes a housing enclosing an X-ray tube that emits the shaped X-ray beam, a plurality of vanes for collimating a plurality of X-ray beams scattered from the object, a plurality of detectors for generating scan data corresponding to the plurality of collimated X-ray beams detected by said plurality of detectors, a processor in communication with a gyroscope and an accelerometer, and an acquisition system in communication with a speaker, a display, said processor and said plurality of detectors. In some embodiments, the method includes using the processor for calculating a plurality of active pixels corresponding to a location of interaction of the shaped X-ray beam on the object; using the processor for calculating a time duration, at each of said plurality of active pixels, for which the shaped X-ray beam is present over each of said plurality of active pixels; and using the processor for generating an image, on said display, of the object after correcting the scan data, at each of said plurality of active pixels, using said time duration.

In some embodiments, the shaped X-ray beam is in the form of a fan beam.

In some embodiments, the hand-held imaging device is swept to scan the object using a coarse scanning pattern to identify at least one anomaly, with reference to the object, prior to calculating said plurality of active pixels, calculating said time duration and generating said image. Optionally, the one anomaly is identified based on a change in audible tone generated by the speaker. Still optionally, a pitch or frequency of said audible tone is proportional to said generated scan data. Optionally, upon identification of said at least one anomaly, the hand-held imaging device is swept to scan the object using a fine scanning pattern for calculating said plurality of active pixels, calculating said time duration and generating said image. Still optionally, the method further includes receiving second data by the processor, wherein said second data is generated by the accelerometer and is indicative of a movement of the shaped X-ray beam being projected on the object and wherein based on said second data using the processor for calculating a plurality of active pixels corresponding to a new location of interaction of the shaped X-ray beam on the object; using the processor for calculating a time duration, at each of said plurality of active pixels, for which the shaped X-ray beam is present over each of said plurality of active pixels; and using the processor for generating an updated image, on said display, of the object after correcting the scan data, at each of said plurality of active pixels, using said time duration. Optionally, the new location is associated with an updated first data generated by the gyroscope, and wherein said updated first data is indicative of a new direction of the shaped X-ray beam being projected on the object.

In some embodiments, the acquisition system sums said detected scan data over a sampling duration of 1 ms.

In some embodiments, a voltage of the X-ray tube ranges between 30 kV and 100 kV.

In some embodiments, a current of the X-ray tube ranges between 0.1 mA and 5 mA.

In some embodiments, the location is associated with a first data generated by the gyroscope, and wherein said first data is indicative of a direction of the shaped X-ray beam being projected on the object.

In some embodiments, the present specification discloses a system for a hand-held imaging device for scanning an object by projecting a shaped X-ray beam, where the device includes a housing having a central longitudinal axis. In some embodiments, the housing includes a plurality of vanes for collimating a plurality of X-ray beams scattered from the object;

a plurality of detectors for generating scan data corresponding to the plurality of collimated X-ray beams detected by said plurality of detectors; a gyroscope; an accelerometer; an acquisition system in communication with a speaker, a display and said plurality of detectors; and a processor in communication with said gyroscope, said accelerometer and said acquisition system. In some embodiments, the processor is configured for calculating a plurality of active pixels corresponding to a location of interaction of the shaped X-ray beam on the object; calculating a time duration, at each of said plurality of active pixels, for which the shaped X-ray beam is present over each of said plurality of active pixels; and generating an image, on said display, of the object after correcting the scan data, at each of said plurality of active pixels, using said time duration.

In some embodiments, the shaped X-ray beam is in the form of a fan beam.

In some embodiments, the hand-held imaging device is swept to scan the object using a coarse scanning pattern to identify at least one anomaly, with reference to the object, prior to said processor calculating said plurality of active pixels, calculating said time duration and generating said image. Optionally, the anomaly is identified based on a change in audible tone generated by the speaker. Still optionally, a pitch or frequency of said audible tone is proportional to said generated scan data. Optionally, upon identification of said at least one anomaly, the hand-held imaging device is swept to scan the object using a fine scanning pattern for calculating said plurality of active pixels, calculating said time duration and generating said image.

In some embodiments, the housing has an upper surface, a base opposite and parallel to said upper surface, a front surface, a rear surface opposite and parallel to said front surface, a first side and a second side opposite and parallel to said first side, and wherein said upper surface has at least one handle. Optionally, the housing is configured as a first cuboid, bearing said front surface, which tapers along the central longitudinal axis into a second cuboid culminating in said rear surface. Optionally, the shaped X-ray beam emerges through an opening at a center of said front surface in a direction substantially perpendicular to said front surface. Optionally, the plurality of detectors are positioned adjacent to and behind said front surface surrounding said opening at the center of said front surface, and wherein said plurality of vanes are positioned in front of said plurality of detectors and behind said front surface.

In some embodiments, the plurality of detectors include four sets of detectors.

In some embodiments, planes of said plurality of vanes are arranged in a direction substantially perpendicular to an orientation of a plane of said fan beam. Optionally, planes of said plurality of vanes are arranged one of substantially parallel to each other, in a substantially diverging orientation with respect to each other, and in a substantially converging orientation with respect to each other.

In some embodiments, the present specification discloses a method for scanning an object by projecting a shaped X-ray beam from a hand-held imaging device. In some embodiments, the device includes a housing enclosing an X-ray tube that emits the shaped X-ray beam, a grid of a plurality of collimator elements for collimating a plurality of X-ray beams scattered from the object, a plurality of detectors for generating scan data corresponding to the plurality of collimated X-ray beams detected by said plurality of detectors, a processor in communication with a gyroscope and an accelerometer, and an acquisition system in communication with a speaker, a display, said processor and said plurality of detectors. In some embodiments, the method includes using the processor for calculating a plurality of active pixels corresponding to a location of interaction of the shaped X-ray beam on the object; using the processor for calculating a time duration, at each of said plurality of active pixels, for which the shaped X-ray beam is present over each of said plurality of active pixels; and using the processor for generating an image, on said display, of the object after correcting the scan data, at each of said plurality of active pixels, using said time duration.

In some embodiments, the shaped X-ray beam is in the form of a cone beam.

In some embodiments, the hand-held imaging device is swept to scan the object using a coarse scanning pattern to identify at least one anomaly, with reference to the object, prior to calculating said plurality of active pixels, calculating said time duration and generating said image. Optionally, the anomaly is identified based on a change in audible tone generated by the speaker. Still optionally, a pitch or frequency of said audible tone is proportional to said generated scan data. Optionally, upon identification of said at least one anomaly, the hand-held imaging device is swept to scan the object using a fine scanning pattern for calculating said plurality of active pixels, calculating said time duration and generating said image. Still optionally, the method further includes receiving second data by the processor, wherein said second data is generated by the accelerometer and is indicative of a movement of the shaped X-ray beam being projected on the object and wherein based on said second data the method includes using the processor for calculating a plurality of active pixels corresponding to a new location of interaction of the shaped X-ray beam on the object; using the processor for calculating a time duration, at each of said plurality of active pixels, for which the shaped X-ray beam is present over each of said plurality of active pixels; and using the processor for generating an updated image, on said display, of the object after correcting the scan data, at each of said plurality of active pixels, using said time duration. Still optionally, the new location is associated with an updated first data generated by the gyroscope, and wherein said updated first data is indicative of a new direction of the shaped X-ray beam being projected on the object.

In some embodiments, the acquisition system sums said detected scan data over a sampling duration ranging between 0.01 ms and 100 ms.

In some embodiments, the acquisition system sums said detected scan data over a sampling duration of 1 ms.

In some embodiments, a voltage of the X-ray tube ranges between 30 kV and 100 kV.

In some embodiments, a current of the X-ray tube ranges between 0.1 mA and 5 mA.

In some embodiments, the location is associated with a first data generated by the gyroscope, and wherein said first data is indicative of a direction of the shaped X-ray beam being projected on the object.

In some embodiments, the present specification discloses a system for a hand-held imaging device for scanning an object by projecting a shaped X-ray beam, where the device includes a housing having a central longitudinal axis and including a grid of a plurality of collimator elements for collimating a plurality of X-ray beams scattered from the object; a plurality of detectors for generating scan data corresponding to the plurality of collimated X-ray beams detected by said plurality of detectors; a gyroscope; an accelerometer; an acquisition system in communication with a speaker, a display and said plurality of detectors; and a processor in communication with said gyroscope, said accelerometer and said acquisition system. In some embodiments, the processor is configured for calculating a plurality of active pixels corresponding to a location of interaction of the shaped X-ray beam on the object; calculating a time duration, at each of said plurality of active pixels, for which the shaped X-ray beam is present over each of said plurality of active pixels; and generating an image, on said display, of the object after correcting the scan data, at each of said plurality of active pixels, using said time duration.

In some embodiments, the shaped X-ray beam is in the form of a cone beam.

In some embodiments, the housing has an upper surface, a base opposite and parallel to said upper surface, a front surface, a rear surface opposite and parallel to said front surface, a first side and a second side opposite and parallel to said first side, and wherein said upper surface has at least one handle. Optionally, the housing is configured as a first cuboid, bearing said front surface, which tapers along the central longitudinal axis into a second cuboid culminating in said rear surface. Optionally, the shaped X-ray beam emerges through an opening at a center of said front surface in a direction substantially perpendicular to said front surface. Optionally, the plurality of detectors are positioned adjacent to and behind said front surface surrounding said opening at the center of said front surface, and wherein said grid is positioned behind said front surface and in front of said plurality of detectors such that at least one of said plurality of detectors is present per said collimator element.

In some embodiments, the grid comprises first and second sets of a plurality of combs, each of said plurality of combs having teeth, wherein the teeth of said first set of combs in a first direction interlock with the teeth of said second set of combs in a second direction, and wherein said second direction is substantially orthogonal to said first direction. Optionally, planes of said teeth are arranged in one of a direction substantially parallel to an orientation of said shaped X-ray beam, substantially parallel to each other, substantially diverging orientation with respect to each other, and substantially converging orientation with respect to each other.

In some embodiments, each of said plurality of detectors maps to an area on the object, wherein said area is defined by a solid angle of said cone beam and an acceptance angle of each of said plurality of collimator elements.

In some embodiments, the present specification discloses a method for scanning an object by projecting a shaped X-ray beam from a hand-held imaging device. In some embodiments, the device includes a housing enclosing an X-ray tube that emits the shaped X-ray beam, a first rotating collimator having a first transmission pattern and a second rotating collimator having a second transmission pattern, said first and second transmission patterns defining said shaped X-ray beam, a plurality of detectors for generating scan data corresponding to a plurality of detected X-ray beams, a processor in communication with a gyroscope and an accelerometer, and an acquisition system in communication with a speaker, a display, said processor and said plurality of detectors. In some embodiments, the method includes using the processor for calculating a plurality of active pixels corresponding to a location of interaction of the shaped X-ray beam on the object; using the processor for calculating a time duration, at each of said plurality of active pixels, for which the shaped X-ray beam is present over each of said plurality of active pixels; and using the processor for generating an image, on said display, of the object after correcting the scan data, at each of said plurality of active pixels, using said time duration.

In some embodiments, the shaped X-ray beam is in the form of a pencil beam. Optionally, the first transmission pattern defines a radial position of said pencil beam while said second transmission pattern defines an azimuthal angle of said pencil beam.

In some embodiments, the hand-held imaging device is swept to scan the object using a coarse scanning pattern to identify at least one anomaly, with reference to the object, prior to calculating said plurality of active pixels, calculating said time duration and generating said image. Optionally, the anomaly is identified based on a change in audible tone generated by the speaker. Still optionally, a pitch or frequency of said audible tone is proportional to said generated scan data. Optionally, upon identification of said at least one anomaly, the hand-held imaging device is swept to scan the object using a fine scanning pattern for calculating said plurality of active pixels, calculating said time duration and generating said image.

In some embodiments, the method further includes receiving second data by the processor, wherein said second data is generated by the accelerometer and is indicative of a movement of the shaped X-ray beam being projected on the object and wherein based on said second data the method includes using the processor for calculating a plurality of active pixels corresponding to a new location of interaction of the shaped X-ray beam on the object; using the processor for calculating a time duration, at each of said plurality of active pixels, for which the shaped X-ray beam is present over each of said plurality of active pixels; and using the processor for generating an updated image, on said display, of the object after correcting the scan data, at each of said plurality of active pixels, using said time duration. Optionally, the new location is associated with an updated first data generated by the gyroscope, and wherein said updated first data is indicative of a new direction of the shaped X-ray beam being projected on the object.

In some embodiments, the acquisition system sums said detected scan data over a sampling duration ranging between 0.01 ms and 100 ms.

In some embodiments, the acquisition system sums said detected scan data over a sampling duration of 1 ms.

In some embodiments, a voltage of the X-ray tube ranges between 30 kV and 100 kV.

In some embodiments, a current of the X-ray tube ranges between 0.1 mA and 5 mA.

In some embodiments, the location is associated with a first data generated by the gyroscope, and wherein said first data is indicative of a direction of the shaped X-ray beam being projected on the object.

In some embodiments, the present specification discloses a system for a hand-held imaging device for scanning an object by projecting a shaped X-ray beam, where the device includes a housing having a central longitudinal axis. In some embodiments, the housing includes a first rotating collimator having a first transmission pattern and a second rotating collimator having a second transmission pattern, said first and second transmission patterns defining said shaped X-ray beam; a plurality of detectors for generating scan data corresponding to a plurality of detected X-ray beams; a gyroscope; an accelerometer; an acquisition system in communication with a speaker, a display and said plurality of detectors; and a processor in communication with said gyroscope, said accelerometer and said acquisition system. In some embodiments, the processor is configured for calculating a plurality of active pixels corresponding to a location of interaction of the shaped X-ray beam on the object; calculating a time duration, at each of said plurality of active pixels, for which the shaped X-ray beam is present over each of said plurality of active pixels; and generating an image, on said display, of the object after correcting the scan data, at each of said plurality of active pixels, using said time duration.

In some embodiments, the shaped X-ray beam is in the form of a pencil beam. Optionally, the first transmission pattern defines a radial position of said pencil beam while said second transmission pattern defines an azimuthal angle of said pencil beam.

In some embodiments, the first and second collimators rotate in lock step with each other, and wherein said first collimator rotates at a first speed while said second collimator rotates at a second speed. Optionally, the second speed is greater than said first speed.

In some embodiments, the first and second collimators are substantially circular disks having differing radii.

In some embodiments, the first and second collimators are substantially circular disks having same radii.

In some embodiments, the first transmission pattern is a slit extending in a spirally curved configuration from a point proximate a center of said first collimator to a point proximate a circumference of said first collimator, and wherein said second transmission pattern is a slit extending radially from a point proximate a center of said second collimator to a point proximate a circumference of said second collimator.

In some embodiments, the housing has an upper surface, a base opposite and parallel to said upper surface, a front surface, a rear surface opposite and parallel to said front surface, a first side and a second side opposite and parallel to said first side, and wherein said upper surface has at least one handle. Optionally, the housing is configured as a first cuboid, bearing said front surface, which tapers along the central longitudinal axis into a second cuboid culminating in said rear surface. Optionally, the shaped X-ray beam emerges through an opening at a center of said front surface in a direction substantially perpendicular to said front surface. Optionally, the plurality of detectors are positioned adjacent to and behind said front surface surrounding said opening at the center of said front surface. Optionally, the first collimator is arranged coaxially in front of said second collimator along a central longitudinal axis of said housing, and wherein said first and second collimators are positioned between said opening of said front surface and an opening of said X-ray tube.

In some embodiments, the present specification discloses a method for scanning an object by projecting a shaped X-ray beam from a hand-held imaging device. In some embodiments, the device includes a housing enclosing an X-ray tube that emits the shaped X-ray beam, a rotating collimator having a transmission pattern defining said shaped X-ray beam, said rotating collimator supported and partially surrounded by an oscillating shaped cradle, a plurality of detectors for generating scan data corresponding to a plurality of detected X-ray beams, a processor in communication with a gyroscope and an accelerometer, and an acquisition system in communication with a speaker, a display, said processor and said plurality of detectors. In some embodiments, the method includes using the processor for calculating a plurality of active pixels corresponding to a location of interaction of the shaped X-ray beam on the object; using the processor for calculating a time duration, at each of said plurality of active pixels, for which the shaped X-ray beam is present over each of said plurality of active pixels; and using the processor for generating an image, on said display, of the object after correcting the scan data, at each of said plurality of active pixels, using said time duration.

In some embodiments, the shaped X-ray beam is in the form of a pencil beam.

In some embodiments, the hand-held imaging device is swept to scan the object using a coarse scanning pattern to identify at least one anomaly, with reference to the object, prior to calculating said plurality of active pixels, calculating said time duration and generating said image. Optionally, the anomaly is identified based on a change in audible tone generated by the speaker. Still optionally, a pitch or frequency of said audible tone is proportional to said generated scan data. Optionally, upon identification of said at least one anomaly, the hand-held imaging device is swept to scan the object using a fine scanning pattern for calculating said plurality of active pixels, calculating said time duration and generating said image.

In some embodiments, the method further includes receiving second data by the processor, wherein said second data is generated by the accelerometer and is indicative of a movement of the shaped X-ray beam being projected on the object and wherein based on said second data the method includes using the processor for calculating a plurality of active pixels corresponding to a new location of interaction of the shaped X-ray beam on the object; using the processor for calculating a time duration, at each of said plurality of active pixels, for which the shaped X-ray beam is present over each of said plurality of active pixels; and using the processor for generating an updated image, on said display, of the object after correcting the scan data, at each of said plurality of active pixels, using said time duration. Optionally, the new location is associated with an updated first data generated by the gyroscope, and wherein said updated first data is indicative of a new direction of the shaped X-ray beam being projected on the object.

In some embodiments, the acquisition system sums said detected scan data over a sampling duration ranging between 0.01 ms and 100 ms.

In some embodiments, the acquisition system sums said detected scan data over a sampling duration of 1 ms.

In some embodiments, a voltage of the X-ray tube ranges between 30 kV and 100 kV.

In some embodiments, a current of the X-ray tube ranges between 0.1 mA and 5 mA.

In some embodiments, the location is associated with a first data generated by the gyroscope, and wherein said first data is indicative of a direction of the shaped X-ray beam being projected on the object.

In some embodiments, the present specification discloses a system for a hand-held imaging device for scanning an object by projecting a shaped X-ray beam, where the device includes a housing having a central longitudinal axis. In some embodiments, the housing includes a rotating collimator having a transmission pattern defining said shaped X-ray beam, said rotating collimator supported and partially surrounded by an oscillating shaped cradle; a plurality of detectors for generating scan data corresponding to a plurality of detected X-ray beams; a gyroscope; an accelerometer; an acquisition system in communication with a speaker, a display and said plurality of detectors; and a processor in communication with said gyroscope, said accelerometer and said acquisition system. In some embodiments, the processor is configured for calculating a plurality of active pixels corresponding to a location of interaction of the shaped X-ray beam on the object; calculating a time duration, at each of said plurality of active pixels, for which the shaped X-ray beam is present over each of said plurality of active pixels; and generating an image, on said display, of the object after correcting the scan data, at each of said plurality of active pixels, using said time duration.

In some embodiments, the shaped X-ray beam is in the form of a pencil beam.

In some embodiments, the collimator rotates at a speed ranging between 100 to 5000 RPM. In some embodiments, the collimator rotates at a speed of 2000 RPM.

In some embodiments, the rotating collimator causes said shaped X-ray beam to sweep a trajectory in a substantially vertical plane such that a focal spot of said shaped X-ray beam is in a plane of said rotating collimator and on a central longitudinal axis of said housing, and wherein said oscillating shaped cradle causes said shaped X-ray beam to sweep left to right, repeatedly, over said substantially vertical plane.

In some embodiments, the collimator is a substantially circular disk having a first radius while said shaped cradle is substantially semi-circular having a second radius, and wherein said second radius is greater than said first radius.

In some embodiments, the collimator is a substantially circular disk having a radius while said shaped cradle is substantially 'U' or 'C' shaped.

In some embodiments, the transmission pattern is an opening at a point between a center and a circumference of said collimator, and wherein said rotating and said oscillating movements together cause said shaped X-ray beam to move in a raster pattern over a two dimensional area of the object.

In some embodiments, the housing has an upper surface, a base opposite and parallel to said upper surface, a front surface, a rear surface opposite and parallel to said front surface, a first side and a second side opposite and parallel to said first side, and wherein said upper surface has at least one handle. Optionally, the housing is configured as a first cuboid, bearing said front surface, which tapers along the central longitudinal axis into a second cuboid culminating in said rear surface. Optionally, the shaped X-ray beam emerges through an opening at a center of said front surface in a direction substantially perpendicular to said front surface. Still optionally, the plurality of detectors are positioned adjacent to and behind said front surface surrounding said opening at the center of said front surface. Still optionally, respective centers of said collimator and said shaped cradle are substantially coaxial with a central longitudinal axis of said housing, and wherein said collimator and said shaped cradle are positioned between said opening of said front surface and an opening of said X-ray tube.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

In some embodiments, the present specification discloses a system for scanning an object by projecting a shaped X-ray beam from a hand-held imaging device, where the device includes a housing enclosing an X-ray tube that emits the shaped X-ray beam, a plurality of detectors for generating scan data, a processor in communication with a gyroscope and an accelerometer, and an acquisition system. In some embodiments, the method includes using the processor for calculating a plurality of active pixels corresponding to a location of interaction of the shaped X-ray beam on the object; using the processor for calculating a time duration, at each of said plurality of active pixels, for which the shaped X-ray beam is present over each of said plurality of active pixels; and using the processor for generating an image, on said display, of the object after correcting the scan data, at each of said plurality of active pixels, using said time duration.

In some embodiments, the shaped X-ray beam is a pencil beam.

In some embodiments, the shaped X-ray beam is a cone beam.

In some embodiments, the shaped X-ray beam is a fan beam.

In some embodiments, the shaped X-ray beam is a single-axis rotating beam.

In some embodiments, the shaped X-ray beam is a dual-axis rotating beam.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

Pencil Beam

Figure 1A:
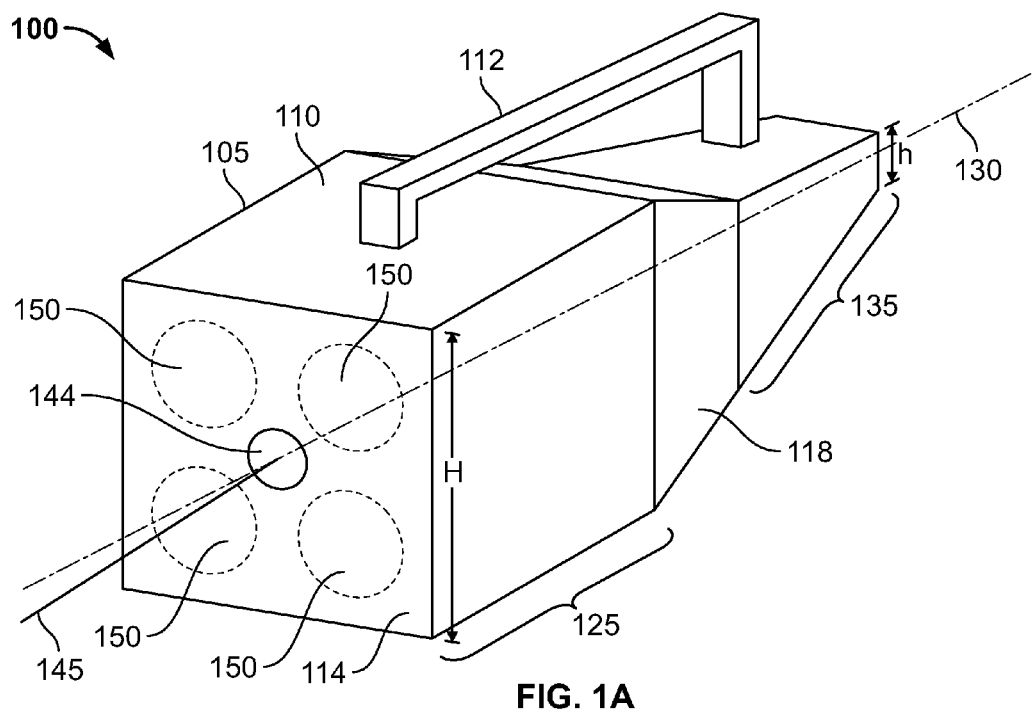
FIG. 1A is a perspective view of a hand-held portable scanning device, in accordance with an embodiment of the present specification.

FIG. 1A illustrates an embodiment of a hand-held portable X-ray based scanning system 100, also referred to as an imaging system or device, for use in screening objects such as, but not limited to, baggage, containers/boxes, and other similar items for threat materials, items or people concealed therein. The system 100 is configured, in one embodiment, in the form of an enclosure or housing 105 having an upper surface 110, a base (not visible in FIG. 1A, but opposite, and substantially parallel to, the upper surface 110), a front surface 114, a rear surface (not visible in FIG. 1A, but opposite, and parallel to, the front surface 114), a first side 118, and a second side (not visible in FIG. 1A, but opposite, and parallel to, the first side 118). In accordance with one embodiment, the size and weight of system 100 is optimized for enabling an operator to conveniently hold and maneuver the housing 105 while scanning an object under inspection. In one embodiment, housing 105 is in the form of a first cuboid 125 (bearing the front surface 114) that tapers, along a central longitudinal axis 130, into a second cuboid 135 culminating in the rear surface. In accordance with an embodiment, a height 'H' of the first cuboid 125 is greater than a height 'h' of the second cuboid 135. It should, however, be appreciated that the shape of the housing 105 can be cylindrical, conical, pyramidal or any other suitable shape in various embodiments. Specifically, in one embodiment, housing 105 is in the form of a first cuboid 125 that attaches, at a back face and along a central longitudinal axis 130, to a first trapezoidal prism 118 that tapers and, at its back face, attaches a second trapezoidal prism 135.

At least one handle 112 is provided on, for example, the upper surface 110 to allow the operator to hold the housing 105 conveniently in one or both hands and manipulate the device 100 to point the front surface 114 towards and at different regions on the object under inspection. In alternate embodiments one or more handles are provided on one or more areas or regions such as the upper surface 110, the base, the first side 118 and/or the second side so that single-handed or two-handed operation of device 100 is facilitated, depending on what is easiest for the operator.

Conventionally, X-rays are generated using a thermionic source of electrons, such as a hot tungsten wire in vacuum. The thermionic electrons are then accelerated in an electric field towards an anode or target at a high electrical potential relative to the electron source. Typically the anode is made from a refractory metal of high atomic number, such as tungsten or molybdenum. When electrons hit the anode at high potential, X-rays are created as the electrons lose energy in the anode material. Typically it is through the photoelectric and Bremsstrahlung interactions by which the electrons lose their energy and so create X-rays. The net result is a broad spectrum of X-ray energies, from close to zero up to the maximum energy of the accelerated electrons.

The principles described above are applicable throughout each of the embodiments described in the present specification and will not be repeated with respect to each embodiment.

Figure 1B:
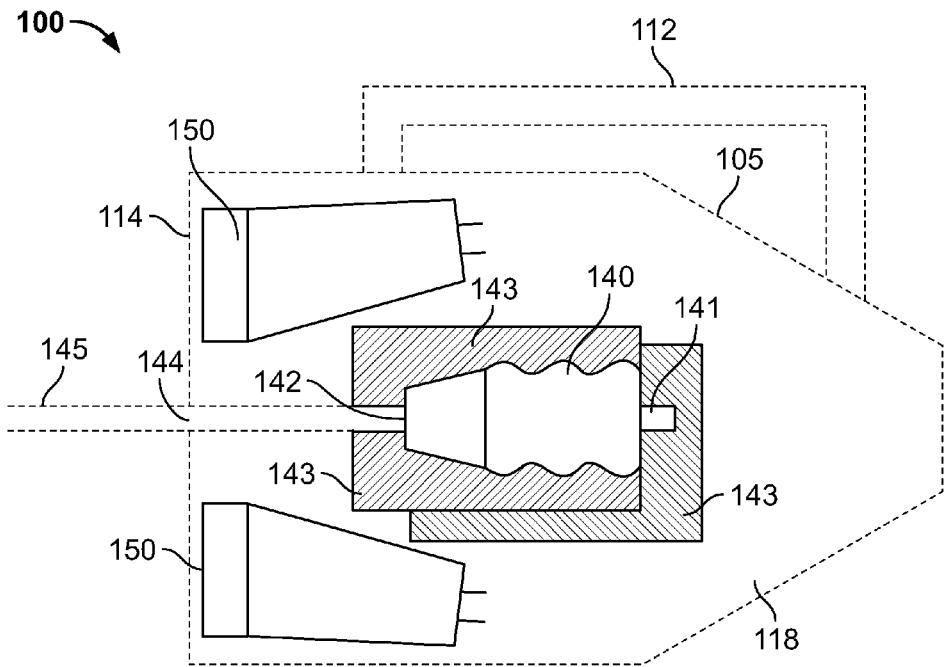
FIG. 1B is a vertical cross-sectional view of the hand-held portable scanning device of FIG. 1A.

Referring now to FIGS. 1A and 1B, the housing 105 comprises an X-ray tube 140 whose anode 141, also referred to as a target, emits a spatially localized X-ray beam 145 through an opening 142, also referred to as an aperture. At least one shield 143, formed of an X-ray absorptive material, such as tungsten or uranium, surrounds and encloses anode 141 to absorb stray radiation emitted from anode 141. Opening 142, defined through shield 143, is provided with a size and thickness which enables opening 142 to act as a collimator in forming or shaping and limiting the X-ray radiation, emitted from anode 141, into a shaped beam of X-rays 145. In one embodiment, X-ray beam 145 is shaped into a pencil beam.

A cathode and heater filament assembly (enclosed within housing 105) is held at a substantial potential difference (using a chargeable battery also enclosed within the housing 105) with reference to anode 141 by a kilovolt power supply (wrapped around at least one tube shielding 143, in one embodiment). This potential difference causes thermionic electrons freed by the heated cathode (heated using the heater filament) to be directed and drawn to anode 141 at sufficiently high velocity to result in the generation of X-ray beam 145.

In accordance with an embodiment, shaped X-ray beam 145 emerges through an opening 144 at the center of front surface 114 of housing 105, in a direction substantially perpendicular to front surface 114. At least one or a plurality of X-ray backscatter detectors 150, also referred to as sensors, are positioned adjacent to and behind front surface 114 such that they surround the area or region of emergence of X-ray beam 145 at opening 144 and cover a substantial area of front surface 114 in order to maximize detected backscatter signal. An embodiment of the present specification comprises four sets of detectors 150. In other embodiments, a different number of detectors 150 may be utilized.

In accordance with an aspect, detectors 150 advantageously comprise high density inorganic scintillators (such as NaI, BGO, LYSO, CsI) coupled to a suitable optical readout such as a photomultiplier tube, an array of semiconductor photomultipliers or an array of photodiodes. Other detector types include inorganic scintillators (such as poly-vinyl toluene) coupled to photomultiplier tubes or room temperature semiconductor detectors (such as CdTe, CdZnTe, TlBr, HgI). As will be evident to one skilled in the art, many detector topologies are possible, such as, but not limited to, square segmented, circular segmented or annular, while the endeavor is to balance cost against complexity and overall detection efficiency. The detector surface adapted to received scattered X-ray radiation is positioned proximate the front surface 114 of housing 105.

Also, detectors 150 can be operated in a plurality of ways. For example, each detector can be operated in a pulse-counting, energy discriminating mode to build up an energy spectrum of the interacting X-rays, whereby these spectra are sampled over short scanning periods to build up a map of count rate and associated energy spectrum for each scatter source point location on the surface of the object under inspection. As an example, assume that the operator is scanning the beam at a rate of 0.2 m/second over the surface of the object and the projected X-ray beam width at the object is 10 mm. Therefore, in an embodiment, the update rate is equal to a movement of half the X-ray beam width (5 mm in this case) corresponding to a dwell time of (5 mm)/(200 mm/s)=25 ms. The energy distribution in the spectrum is analyzed to find those X-rays of higher energy which are more likely to have come from a greater depth in the object compared to those at lower energy which are more likely to have come from the surface of the object. It is also possible to separate out those photons whose energy is higher than the maximum emitted from the X-ray tube since these are either summed events (in which more than one scattered X-ray interacted in the detector at the same time) or are events due to naturally occurring background radiation. In either case, these are used to compensate for artifacts that would otherwise be present in the signal data.

It should be noted that the maximum energy of the X-rays produced by X-ray tube 140 determines the ability of these X-rays to penetrate into the object under inspection—that is, the higher the maximum X-ray energy, the more penetration can be achieved. Similarly, the higher the energy of the scattered X-ray photon, the more likely it is to escape through the object under inspection back to an X-ray detector 150. Therefore, in accordance with an aspect it is desirable to have high X-ray energy to maximize depth of inspection within the object.

To improve signal quality, device 100 of the present specification maximizes the number of scattered X-rays that are detected within a given signal integration or sampling period. The number of scattered X-rays for a given type of object under inspection is dependent on the number of X-rays that are incident on the object under inspection directly from the X-ray source. In the case of a fixed tube voltage, it is the anode current that affects the size of the scattered X-ray signal—that is, the higher the anode current, the greater the scattered signal. Most detection systems, such as the detectors 150, are operated close to the Gaussian point whereby the variance in the signal is equal to the mean value of the signal. For example, if the mean number of scattered X-rays reaching the detector in a certain counting period were 100, then the variance would be 100 and the standard deviation would be square root of 100 (=10). Signal-to-noise ratio (SNR) is defined as mean divided by standard deviation, therefore, SNR in this example would be 100/10=10.

Therefore, in a preferred embodiment, device 100 has high X-ray tube voltage (to improve penetration performance) and high anode current (to improve signal-to-noise ratio in the scattered X-ray signal). However, such a combination of factors will result in a device which is likely to be heavy due to the physical size of the X-ray tube components (to provide suitable clearance and creepage distance in the high voltage components) and the associated radiation shielding that will be needed to collimate the primary shaped beam and to shield the operator and radiation detectors from stray radiation from the X-ray tube target. Therefore, in various embodiments the tube voltage of the X-ray tube 140 ranges between 30 kV and 100 kV with tube currents ranging between 0.1 mA and 5 mA.

Figure 1C:
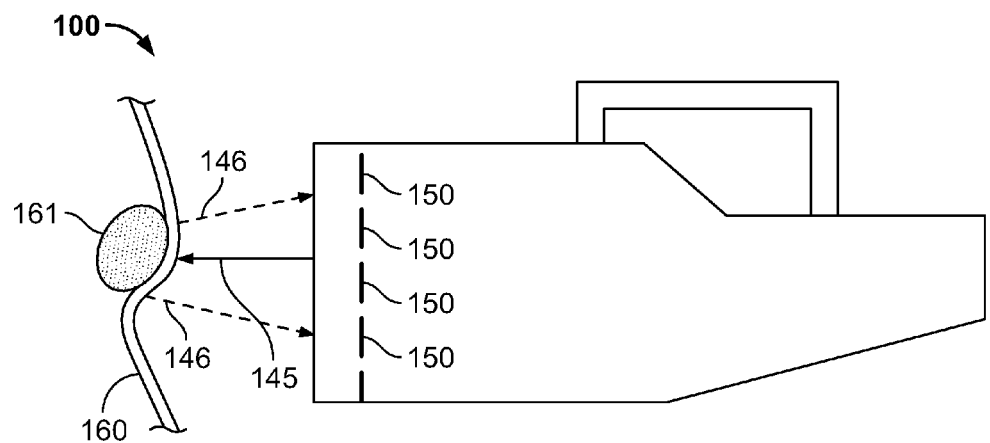
FIG. 1C illustrates the hand-held portable scanning device of the present specification projecting an X-ray beam over an object under inspection, in an embodiment.

During operation, as shown in FIG. 1C, shaped X-ray beam 145 interacts with an object 160 under inspection, to produce scattered X-rays 146. As shown, object 160 conceals therein, an item, person or material 161. Scattered X-rays 146 are detected by the detectors 150 to produce scan data signal whose intensity is related to the effective atomic number (Z) near to the surface of object 160.

Compton scattering describes the interaction of an X-ray photon with an electron that is generally thought of as being at rest. Here, the angle of the exit X-ray photon is related to the direction of the incoming X-ray photon according to the Compton scattering equation:

$$\lambda' - \lambda = \frac{h}{m_e c}(1 - \cos(\theta))$$

where λ=incident photon energy, λ'=exit photon energy, me=mass of the electron and θ=angle between incident and exit photon directions. Thus, the energy of the scattered X-ray is always less than the incident X-ray, the energy being dependent on both the scattering angle and the incident X-ray photon energy.

The above principles related to Compton scattering described here are applicable throughout each of the embodiments described in the present specification and will not be repeated with respect to each embodiment.

Fan Beam

Figure 2A:
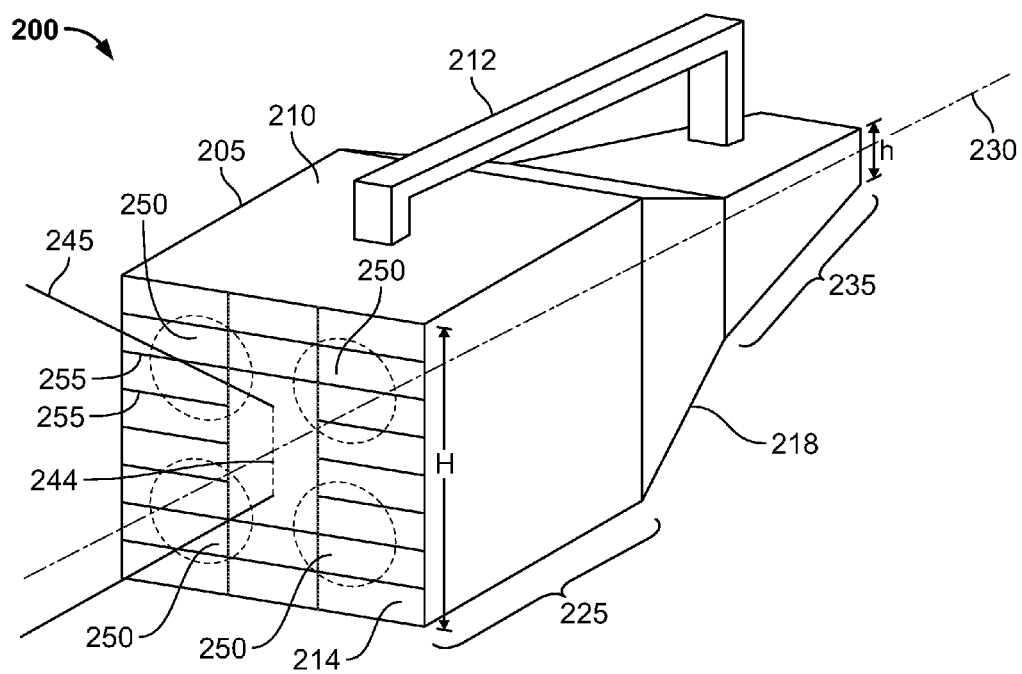
FIG. 2A is a perspective view of a hand-held portable scanning device, in accordance with another embodiment of the present specification.

FIG. 2A illustrates another embodiment of a hand-held portable X-ray based scanning system 200, also referred to as an imaging system or device, for use in screening objects such as, but not limited to, baggage, containers/boxes, and other items for threat materials, items or people concealed therein. In embodiments, components of system 200, such as—a housing 205, an upper surface 210, a base, a handle 212, a front surface 214, a rear surface, a first side 218, a second side, a first cuboid 225, a central longitudinal axis 230, and a second cuboid (or trapezoidal prism) 235—are configured similar to corresponding components described above in context of FIG. 1A. These components, and the associated variations, are not described herein as they have been described in detail above.

Figure 2B:
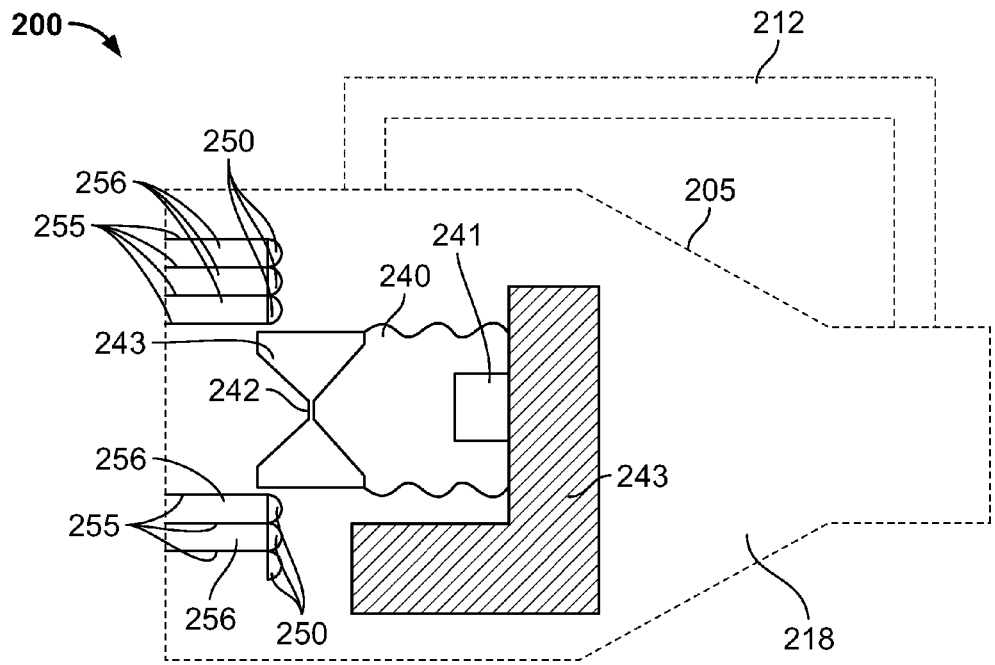
FIG. 2B is a vertical cross-sectional view of the hand-held portable scanning device of FIG. 2A.

Referring now to FIGS. 2A and 2B, housing 205 comprises an X-ray tube 240 whose anode 241, also referred to as a target, emits a spatially localized X-ray beam 245 through an opening 242, also referred to as an aperture. A shield 243, formed of an X-ray absorptive material, such as tungsten or uranium, surrounds anode 241 so as to absorb stray radiation emitted from anode 241. Opening 242 is provided with a size and thickness which enables opening 242 to act as a collimator in forming or shaping and limiting the X-ray radiation, emitted from anode 241, into a shaped beam of X-rays 245. In one embodiment, X-ray beam 245 is fan shaped.

A cathode and heater filament assembly (not shown) may be configured, similar to embodiments described in above relation to the pencil beam embodiment. Similarly, energy of the X-rays and signal quality can be maintained in a manner described above in context of the pencil beam embodiments.

A plurality of collimator vanes, blades, fins or plates 255 are positioned in front of detectors 250 and behind front surface 214, resulting in the formation of a plurality of collimation elements 256 between adjacent collimator vanes 255. In one embodiment, the planes of the plurality of collimator vanes 255 are arranged or configured in a direction substantially perpendicular to the orientation of shaped X-ray beam 245 (that is, to the plane of fan beam 245) or substantially perpendicular to the front surface of the housing. In some embodiments, plurality of collimator vanes 255 are arranged in a parallel configuration, wherein planes of vanes 255 are substantially parallel to each other, such that a vertical dimension, such as height, of a vertical region is viewed through collimators 255 to be of the same size as the extent or height 'H' of front surface 214. In some embodiments, collimator vanes 255 are alternatively arranged in a focused configuration, wherein the planes of vanes 255 together form a diverging or converging orientation, such that collimator vanes 255 view either a smaller or larger of the vertical dimension, such as height, of the vertical region than the extent or the height 'H' of front surface 214.

In various embodiments, detectors 250 are arranged behind collimator vanes 255 such that at least one of detectors 250 is present per collimation element 256 in order to create a one-dimensional linear image.

Figure 2C:
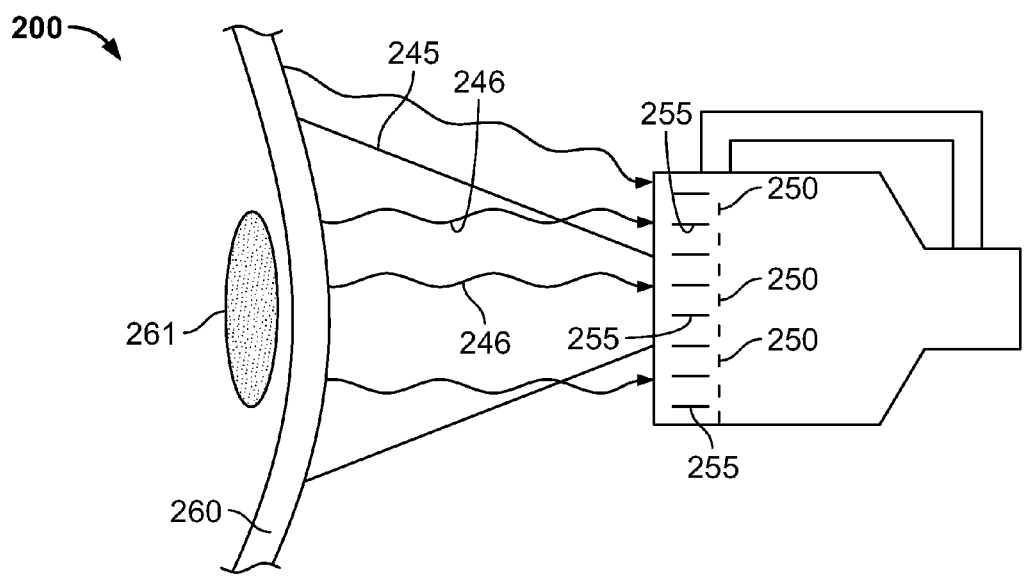
FIG. 2C illustrates the hand-held portable scanning device of the present specification projecting an X-ray beam over an object under inspection, in an embodiment.

During operation, as shown in FIG. 2C, shaped X-ray beam 245 interacts with an object 260 under inspection, to produce scattered X-rays 246. As shown, object 260 conceals therein, an item, person or material 261. Scattered X-rays 246 are collimated by the plurality of collimator vanes 255 and are then detected by detectors 250 to produce scan data signal whose intensity is related to the effective atomic number (Z) near to the surface of object 260. In accordance with an embodiment, each detector 250 maps to a specific focus area (of the object 260) which is defined by a width of X-ray fan beam 245 and an acceptance angle of the individual collimator vanes 255.

Cone Beam

Figure 3A:
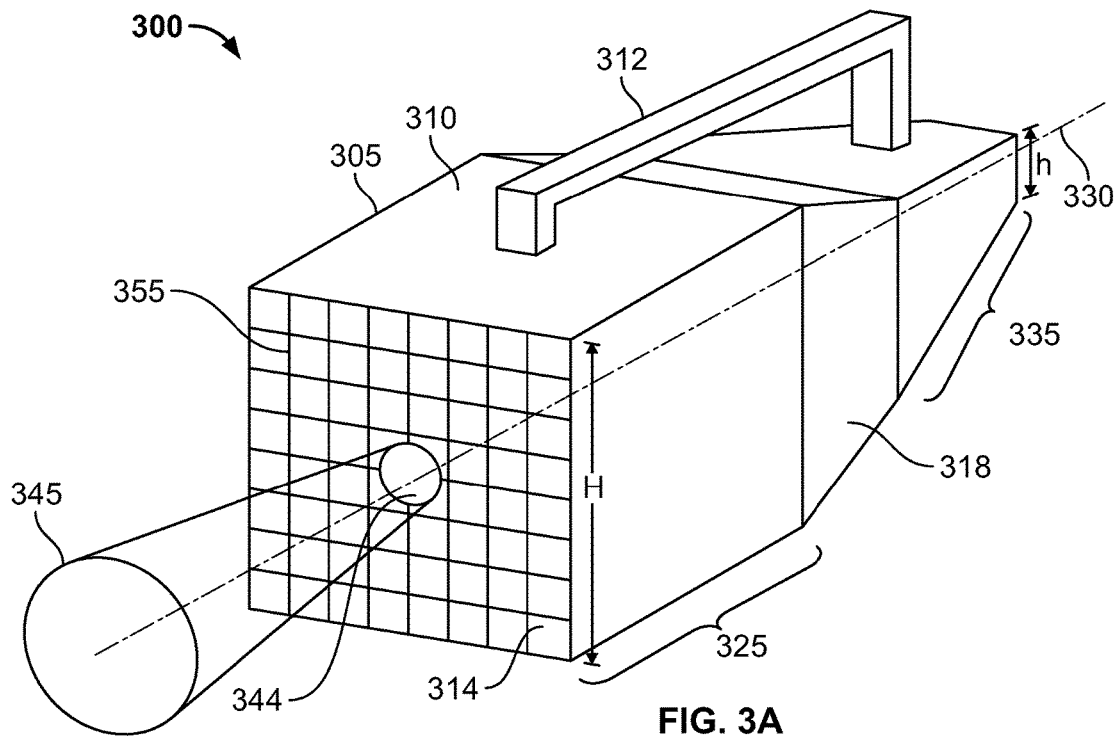
FIG. 3A is a perspective view of a hand-held portable scanning device, in accordance with another embodiment of the present specification.

FIG. 3A illustrates another embodiment of a hand-held portable X-ray based scanning system 300, also referred to as an imaging system or device, for use in screening objects such as, but not limited to, baggage, containers/boxes, and other similar items for threat materials, items or people concealed therein. In embodiments, components of system 300, such as—a housing 305, an upper surface 310, a base, a handle 312, a front surface 314, a rear surface, a first side 318, a second side, a first cuboid 325, a central longitudinal axis 330, and a second cuboid (or trapezoidal prism) 335—are configured similar to corresponding components described above in context of FIG. 1A. These components, and associated variations, are not described herein as they have been described in detail above.

Figure 3B:
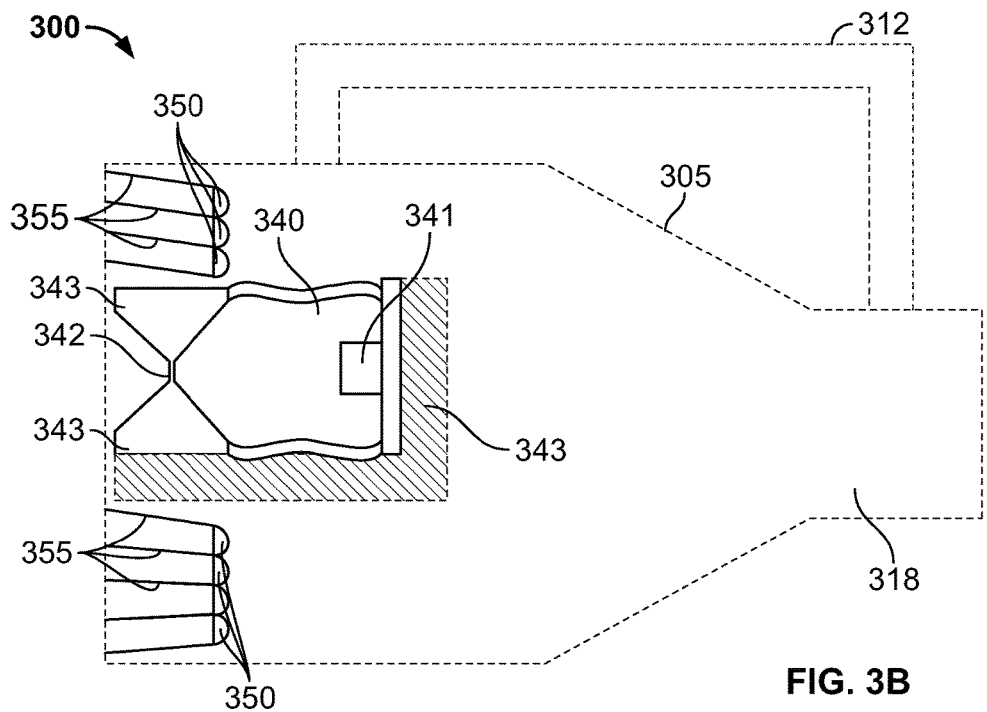
FIG. 3B is a vertical cross-sectional view of the hand-held portable scanning device of FIG. 3A.

Referring now to FIGS. 3A and 3B, housing 305 comprises an X-ray tube 340 whose anode 341, also referred to as a target, emits a spatially localized X-ray beam 345 through an opening 342, also referred to as an aperture. Housing 305 may include corresponding components such as a shield 343, configured in a manner disclosed above in context of FIGS. 1A and 1B. In one embodiment, X-ray beam 345 is cone shaped.

A cathode and heater filament assembly may be configured, similar to embodiments described in above relation to the pencil beam embodiment.

In accordance with an embodiment, shaped X-ray beam 345 emerges through an opening 344 at the center of front surface 314, in a direction substantially perpendicular to front surface 314. A plurality of X-ray backscatter detectors 350 are configured and operated similar to detectors 150 already described in context of FIGS. 1A and 1B. As shown in FIG. 3E, in accordance with an embodiment, an array of 'm' rows×'n' columns of detectors 350 are arranged onto a modular daughter card 351 with a single signal control and readout cable 352 to form a sensing module 353.

Similarly, the energy of the X-rays and signal quality can be maintained in a manner described above in context of the pencil beam embodiments.

Referring now to FIGS. 3A, 3D through 3F, in accordance with an embodiment of the present specification, a collimator grid 355 is positioned in front of detectors 350 and behind front surface 314. Collimator grid 355 comprises a plurality of combs 365a, 365b, made of a suitable attenuating material (such as tungsten, molybdenum or steel), each of plurality of combs 365a, 365b including a plurality of teeth 370a, 370b. In accordance with an embodiment, plurality of combs 365a, 365b are assembled or arranged such that teeth 370a of a first set of combs 365a in a first direction 371a interlock with teeth 370b of a second set of combs 365b in a second direction 371b to thereby generate the collimator grid 355 having a plurality of grid collimators or collimator elements 374. In one embodiment, second direction 371b is generally or approximately traverse or orthogonal to first direction 371a. In accordance with an embodiment, the first set comprises 'm' number of combs 365a while the second set comprises 'n' number of combs 365b to generate a collimator grid 355 that has 'm×n' matrix of substantially rectangular grid collimators 374 at top surface 375.

In one embodiment, the planes of teeth 370a, 370b, forming the grid collimators or collimator elements 374, are in a direction substantially parallel to the orientation of the shaped X-ray beam 345 (that is, cone shaped beam 345) or perpendicular to the front surface of the housing. In some embodiments, the plurality of grid collimators or collimator elements 374 are arranged in a parallel configuration, wherein the planes of teeth 370a, 370b are substantially parallel to each other, such that a vertical dimension, such as height, of a vertical region is viewed through the collimators 374 to be of the same size as the extent or height 'H' of front surface 314. In some embodiments, the plurality of grid collimators or collimator elements 374 are alternatively arranged in a focused configuration, wherein the planes of teeth 370a, 370b together form a diverging or converging orientation, such that the collimator elements 374 view either a smaller or larger of the vertical dimension, such as height, of the vertical region than the extent or the height 'H' of front surface 314. In still various embodiments, the plurality of grid collimators or collimator elements 374 is arranged in a combination of parallel and focused configurations.

In various embodiments, detectors 350 are arranged behind the interlocking collimator structure or collimator grid 355 such that at least one of detectors 350 is present per collimator element or grid collimator 374 in order to create a two-dimensional scan image. As shown in FIG. 3F, collimator grid 355 is coupled to sensing module 353 (comprising the detector module 350 coupled to the daughter card 351 with the signal control and readout cable 352) such that the array of 'm x n' detectors 350 are positioned behind grid 355.

Figure 3C:
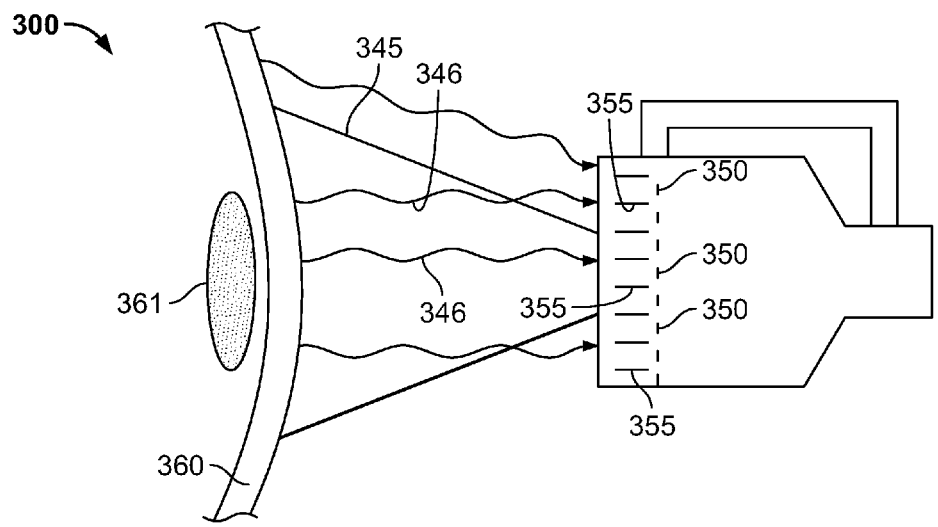
FIG. 3C illustrates the hand-held portable scanning device of the present specification projecting an X-ray beam over an object under inspection, in an embodiment.
Figure 3D:
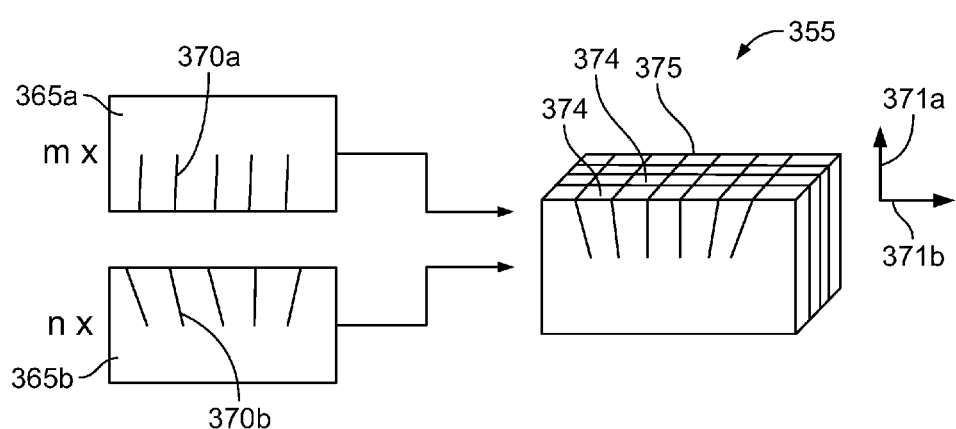
FIG. 3D illustrates a collimator grid fabricated by assembling or arranging a plurality of combs having a plurality of teeth, in accordance with an embodiment.
Figure 3E:
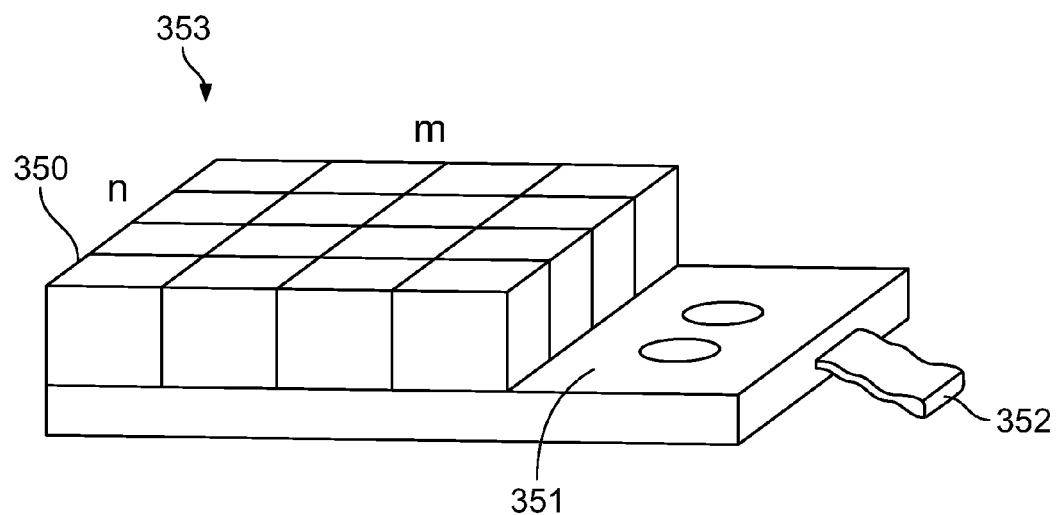
FIG. 3E illustrates a sensing module formed by coupling an array of detectors to a card with a single signal control and readout cable, in accordance with an embodiment.
Figure 3F:
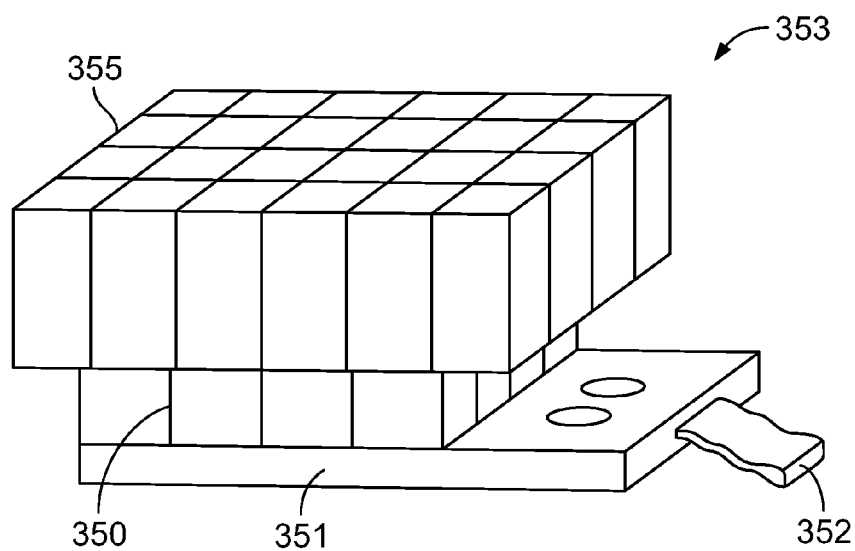
FIG. 3F illustrates a collimator grid coupled to a sensing module, in accordance with an embodiment.

During operation, as shown in FIG. 3C, shaped X-ray beam 345 interacts with an object 360 under inspection to produce scattered X-rays 346. As shown, object 360 conceals therein, an item or material 361. Scattered X-rays 346 is collimated by the plurality of grid collimators or collimator elements 374 and is then detected by the detectors 350 to produce scan data signal whose intensity is related to the effective atomic number (Z) near to the surface of object 360. In accordance with an embodiment, each detector 350 maps to a specific focus area (of the object 360) which is defined by a solid angle of X-ray cone beam 345 and an acceptance angle of the individual collimator elements or grid collimators 374.

Conventional backscatter imaging systems typically use a tightly collimated pencil beam of X-rays and an un-collimated large area detector (referred to as "pencil beam geometry") compared to the use of the collimated cone-shaped beam of X-rays and collimated detectors (referred to as "cone beam geometry") in accordance with an aspect of the present specification. With reference to FIG. 3A, the handheld device of the present specification has, in one embodiment, an outer diameter of 192 mm (considering a circular cross-section of the housing 105) of front surface 314 and is located at a distance of 100 mm from the object under inspection. Detector element 350 is, in an embodiment, 3 mm×3 mm with the X-ray source (X-ray tube 140) located a further 30 mm behind detector array 350 to provide room for radiation shielding around the source. In this embodiment, a total of 4096 detector elements are employed (to create a 64 pixel by 64 pixel image) with an equivalent dwell time of 500 microseconds for pencil beam geometry.

To establish the relative efficiency of the pencil beam versus cone beam configuration, it is useful to calculate the relative solid angles of the whole detector face (pencil beam) and of a single detector to the equivalent inspection area as scanned by the pencil beam (for the cone beam case). This calculation shows that the solid angle for the collimated detector (used in cone beam geometry) is 290 times smaller than for the whole detector face (used in pencil beam geometry).

Taking the assumed pencil beam dwell time of 500 microseconds and multiplying by the number of pixel locations to form an image (4096 in this case) yields an estimated image formation time in pencil beam geometry of 2 seconds. The calculation in the case of the cone beam geometry of the present specification suggests that the dwell time should be 290 times longer than for the pencil beam case to achieve equivalent image statistics, but with a single exposure since all pixel data is collected in parallel. Also, in the case of the cone beam geometry, the image exposure time is more than 50% less than an equivalent pencil beam. This yields an image exposure time in a range of 0.03 seconds 0.1 seconds. Therefore, near real-time two-dimensional image inspection is possible using Compton backscatter inspection in the cone beam geometry of the present specification.

Single-Axis Rotating Beam

Figure 4A:
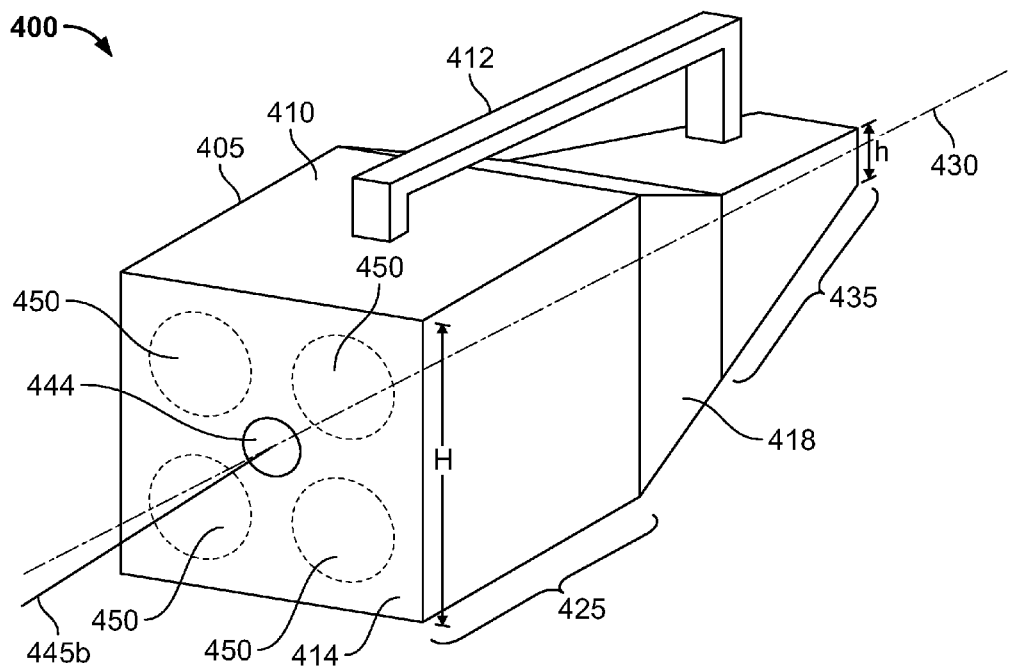
FIG. 4A is a perspective view of a hand-held portable scanning device, in accordance with yet another embodiment of the present specification.

FIG. 4A illustrates an embodiment of a hand-held portable X-ray based scanning system 400, also referred to as an imaging system or device, for use in screening objects such as, but not limited to, baggage, containers/boxes, and other similar items for threat materials, items or people concealed therein. In embodiments, components of system 400, such as—a housing 405, an upper surface 410, a base, a handle 412, a front surface 414, a rear surface, a first side 418, a second side, a first cuboid 425, a central longitudinal axis 430, and a second cuboid (or trapezoidal prism) 435—are configured similar to corresponding components described above in context of FIG. 1A. These components, and associated variations, are not described herein as they have been described in detail above.

Figure 4B:
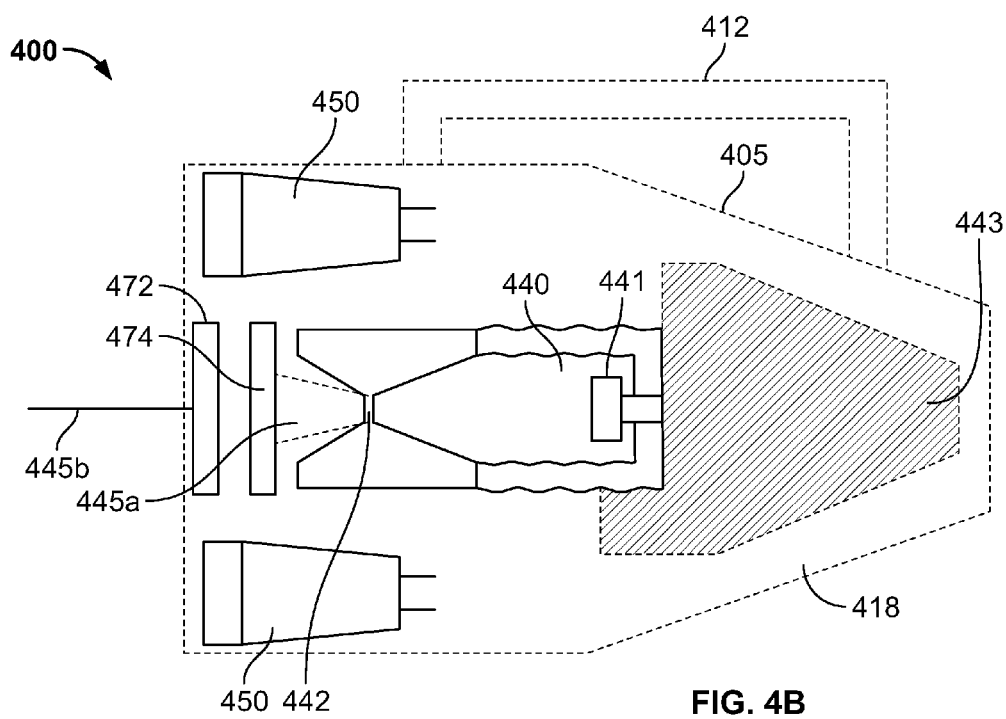
FIG. 4B is a vertical cross-sectional view of the hand-held portable scanning device of FIG. 4A.
Figure 4C:
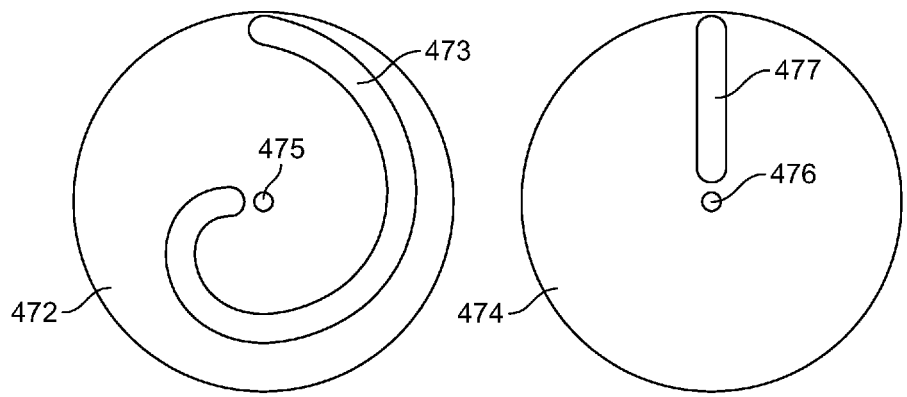
FIG. 4C illustrates first and second collimator disks having first and second transmission patterns, respectively, in accordance with an embodiment.

Referring now to FIGS. 4A and 4B, housing 405 comprises an X-ray tube 440 whose anode 441, also referred to as a target, emits a spatially localized X-ray beam 445a through an opening 442, also referred to as an aperture. A shield 443, formed of an X-ray absorptive material, such as tungsten or uranium, surrounds anode 441 to absorb stray radiation emitted from anode 441. Opening 442 is defined through a highly absorbing block or material (typically tungsten, steel and/or lead) to limit the X-ray radiation, emitted from anode 441, and allow the X-ray radiation to emanate from X-ray tube 440 in the form of beam 445a of X-rays. A cathode and heater filament assembly may be configured, similar to embodiments described in above relation to the pencil beam embodiment.

In accordance with an embodiment of the present specification, X-ray beam 445a is collimated by a collimator assembly 470, enclosed within housing 405, to generate a shaped X-ray beam 445b. In one embodiment, X-ray beam 445b is shaped into a pencil beam. In accordance with an embodiment, shaped X-ray beam 445b emerges through an opening 444 at the center of front surface 414, in a direction substantially perpendicular to front surface 414. A plurality of X-ray backscatter detectors 450 are positioned adjacent to and behind front surface 414 such that they surround the area or region of emergence of X-ray beam 445b at opening 444 and cover a substantial area of front surface 414 in order to maximize detected backscatter signal. An embodiment of the present specification comprises four sets of detectors 450, also referred to as sensors.

An embodiment of collimator assembly 470 comprises a first collimator 472, also referred to as a first limiting element, arranged coaxially in front of a second collimator 474, also referred to as a second limiting element. In one embodiment first and second collimators 472, 474 are positioned between openings 443 and 444 such that collimator assembly 470 defines, shapes, or forms X-ray beam 445a into the shaped X-ray beam 445b.

Referring now to FIGS. 4A through 4F, in one embodiment, first and second collimators 472, 474 are substantially circular disks having differing or same radii. In an embodiment, the respective centers of the first and second collimators 472, 474 are coaxial with the central longitudinal axis 430 of housing 405. First collimator 472 has a first transmission pattern in the form of a through slit 473 extending in a spirally curved configuration from a point proximate center 475 to a point proximate the circumference of element 472. Second collimator 474 has a second transmission pattern in the form of through slit 477 extending radially from a point proximate center 476 to a point proximate the circumference of element 474. Thus, when two collimators 472, 474 are concurrently rotating, the respective first and second transmission patterns or slits 473, 477 generate or define the scanning X-ray pencil beam 445b across the surface of the object under inspection.

Figure 4D:
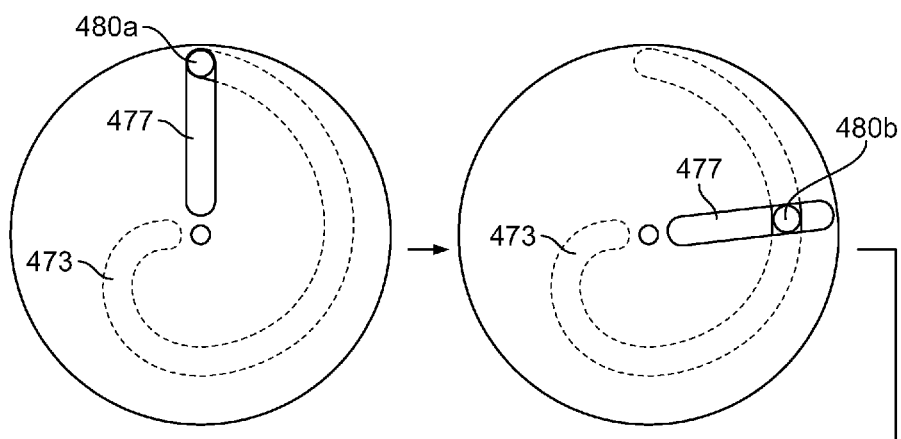
FIG. 4D illustrates various exemplary positions of a moving or sweeping pencil X-ray beam defined by first and second transmission patterns of the first and second collimator disks shown in FIG. 4C.
Figure 4D:
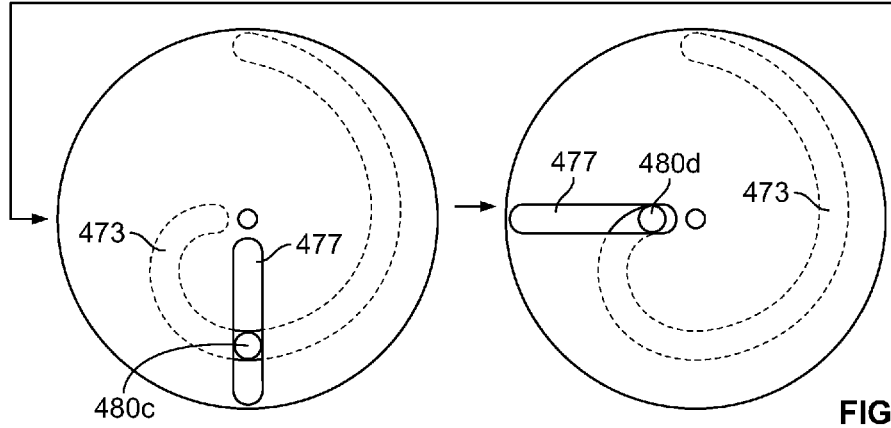

In accordance with an embodiment, the first transmission pattern 473 defines a radial position of pencil beam 445b while the second transmission pattern 477 defines an azimuthal angle of pencil beam 445b. For example, as shown in FIG. 4D, when collimators 472, 474 (the two collimator disks 472, 474 are visible as a single disk since they are shown overlapping each other in FIG. 4D) are rotated relative to each other the position of pencil beam 445b moves or sweeps from a position 480a at the circumference to a position 480d at the coaxial centers 475, 476 (of the collimators 472, 474) through intermediate positions 480b and 480c.

Figure 4E:
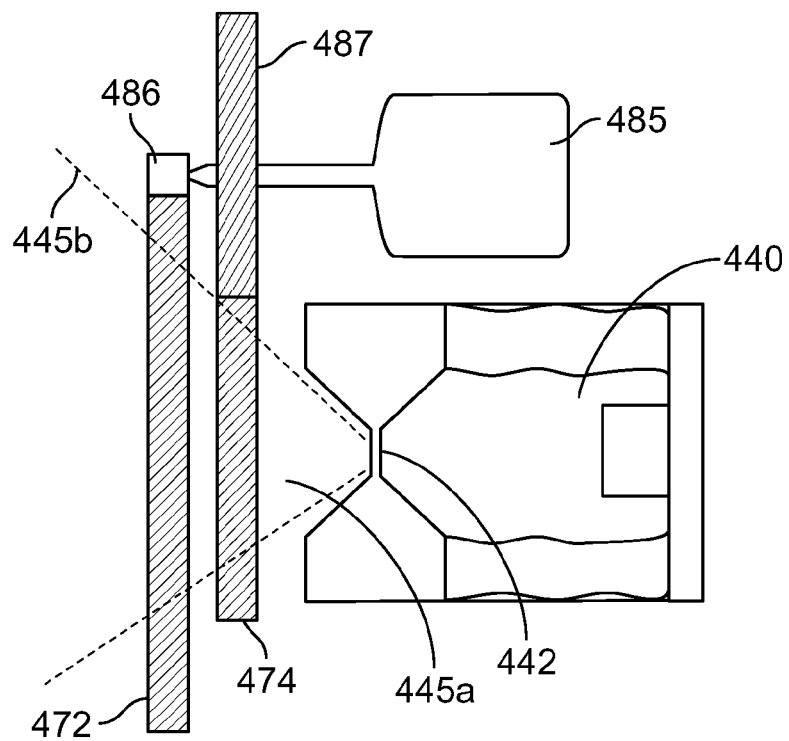
FIG. 4E illustrates a motor driven assembly of first and second gears which, in turn, rotate the first and second collimator disks, shown in FIG. 4C.
Figure 4F:
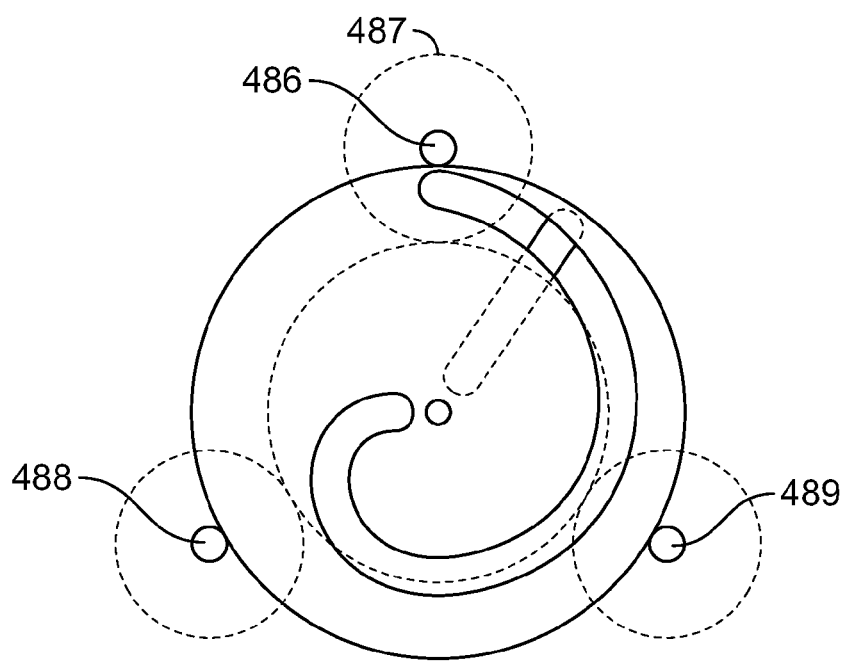
FIG. 4F illustrates two sets of free running drive wheels or gears used to support the first and second collimator disks, shown in FIG. 4C.

FIG. 4E illustrates a motor 485 driving the first and second collimators 472, 474 using a first and a second gear or drive wheels 486, 487 respectively. As would be evident to those of ordinary skill in the art, gears 486, 487, also referred to as drive wheels, engage with mating gear teeth fabricated on the respective circumferences of two collimator disks 472, 474. In accordance with an embodiment, first and second gears 486, 487 rotate the collimator disks 472, 474 such that two collimators 472, 474 are in lock step with each other but rotate at varying speeds to form beam 445a into the shaped X-ray beam 445b. In one embodiment, collimator disk 474 rotates more quickly compared to the speed of rotation of collimator disk 472. In one embodiment, collimator disk 472 rotates more quickly compared to the speed of rotation of collimator disk 474. In one embodiment, the drive wheel or gears 486, 487 affixed to a common spindle (not visible) are driven by motor 485 to rotate collimator disks 472, 474 while two sets of additional free running wheels 488, 489 (not driven by motor 485), shown in FIG. 4F, support collimator disks 472, 474 to maintain their position or orientation relative to X-ray tube 440 (or opening 442).

A plurality of X-ray backscatter detectors 450 are configured and operated similar to detectors 150 already described in context of FIGS. 1A and 1B. Similarly, energy of the X-rays and signal quality can be maintained in a manner described earlier in context of the pencil beam embodiments.

Figure 4G:
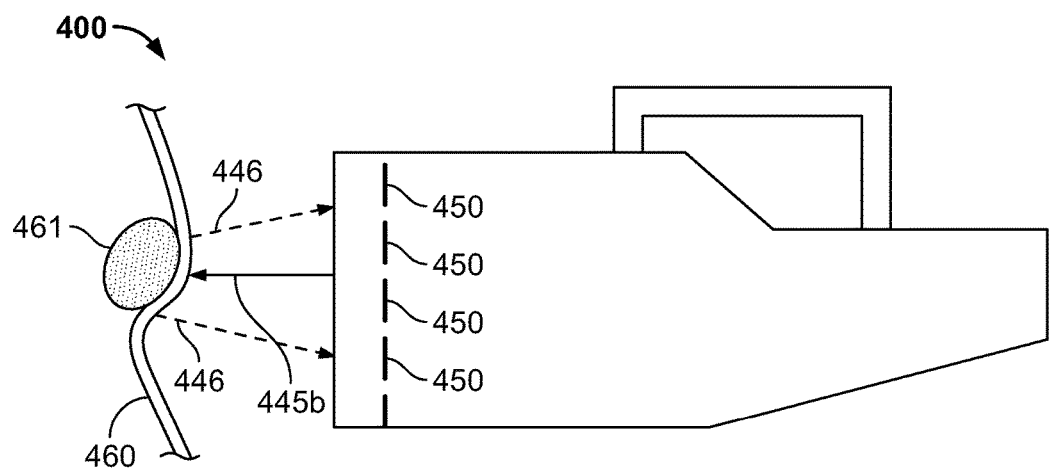
FIG. 4G illustrates the hand-held portable scanning device of the present specification projecting an X-ray beam over an object under inspection, in an embodiment.

During operation, as shown in FIG. 4G, shaped X-ray beam 445b interacts with an object 460 under inspection to produce scattered X-rays 446. As shown, object 460 conceals therein, an item or material 461. Scattered X-rays 446 are then detected by detectors 450 to produce scan data signal whose intensity is related to the effective atomic number (Z) near to the surface of object 460. Any one or more of the aforementioned collimation systems can be combined with this single-axis rotating beam embodiment to effectively detect scattered X-rays.

Dual-Axis Rotating Beam

Figure 5A:
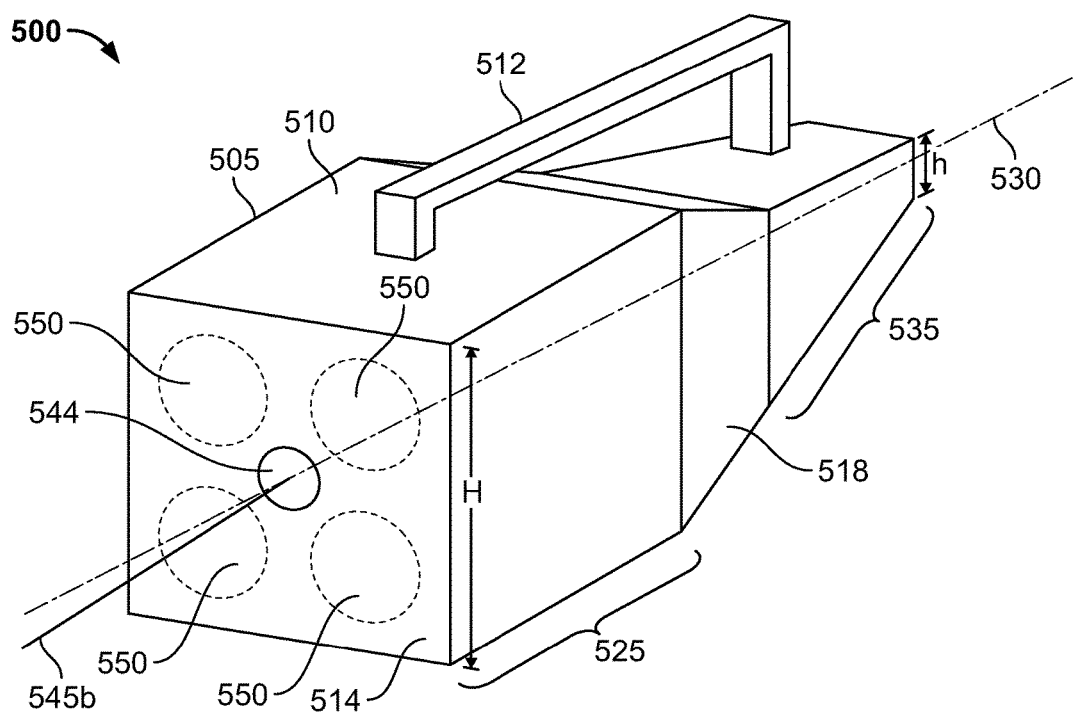
FIG. 5A is a perspective view of a hand-held portable scanning device, in accordance with still another embodiment of the present specification.

FIG. 5A illustrates another embodiment of a hand-held portable X-ray based scanning system 500, also referred to as an imaging system or device, for use in screening objects such as, but not limited to, baggage, containers/boxes, and other similar items for threat materials, items or people concealed therein. In embodiments, components of system 500, such as—a housing 505, an upper surface 510, a base, a handle 512, a front surface 514, a rear surface, a first side 518, a second side, a first cuboid 525, a central longitudinal axis 530, and a second cuboid (or trapezoidal prism) 535—are configured similar to corresponding components described above in context of FIG. 1A. These components, and associated variations, are not described here to avoid repetition.

Figure 5B:
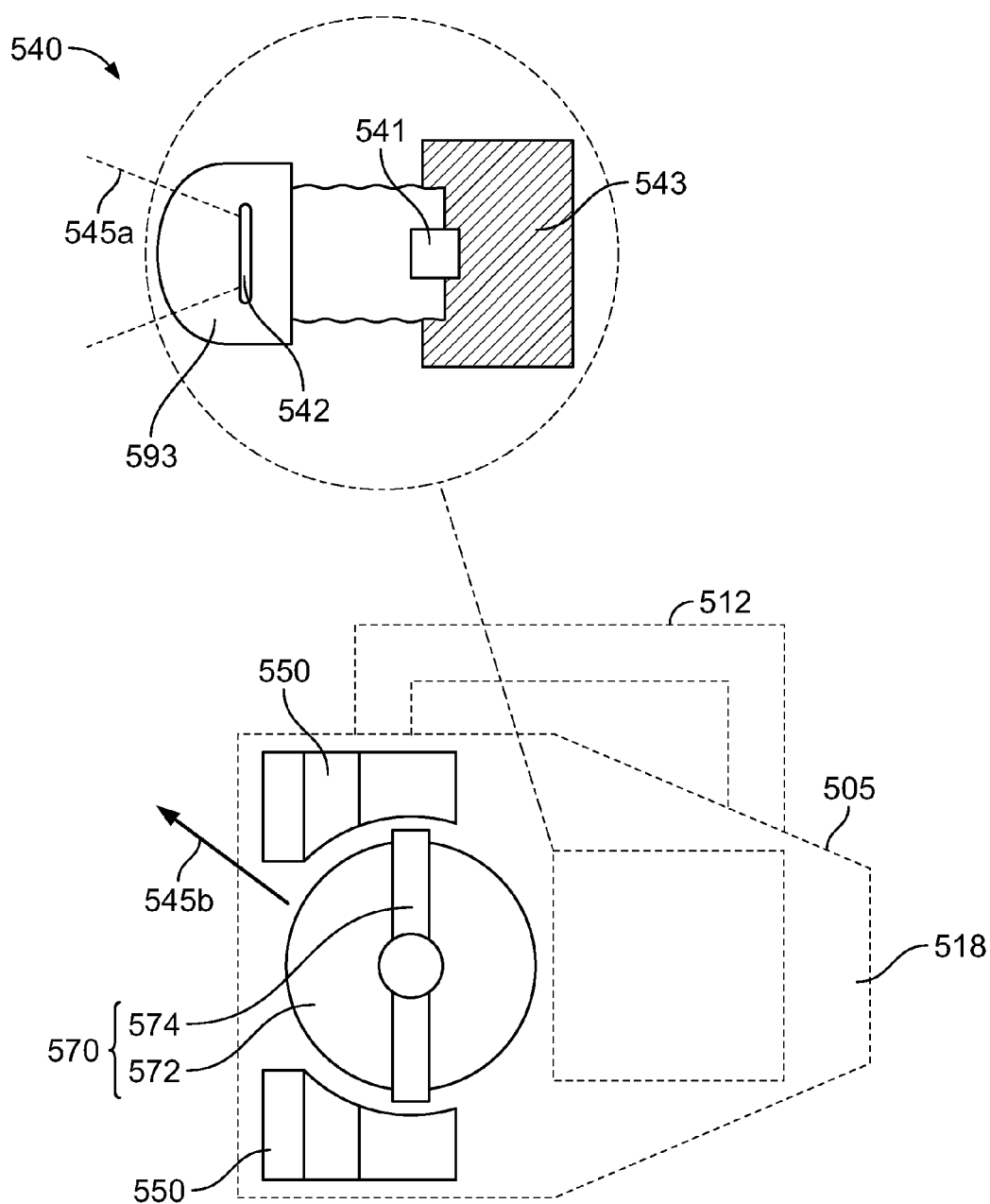
FIG. 5B is a vertical cross-sectional view of the hand-held portable scanning device of FIG. 5A.
Figure 5C:
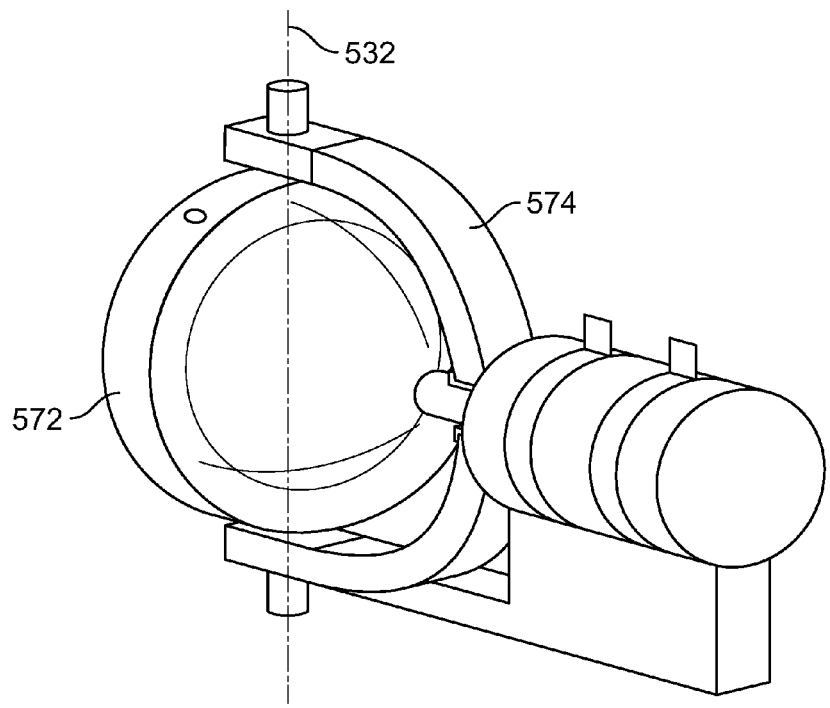
FIG. 5C is a front view of a motor driven collimator assembly comprising a collimator and support or cradle, in accordance with an embodiment.
Figure 5D:
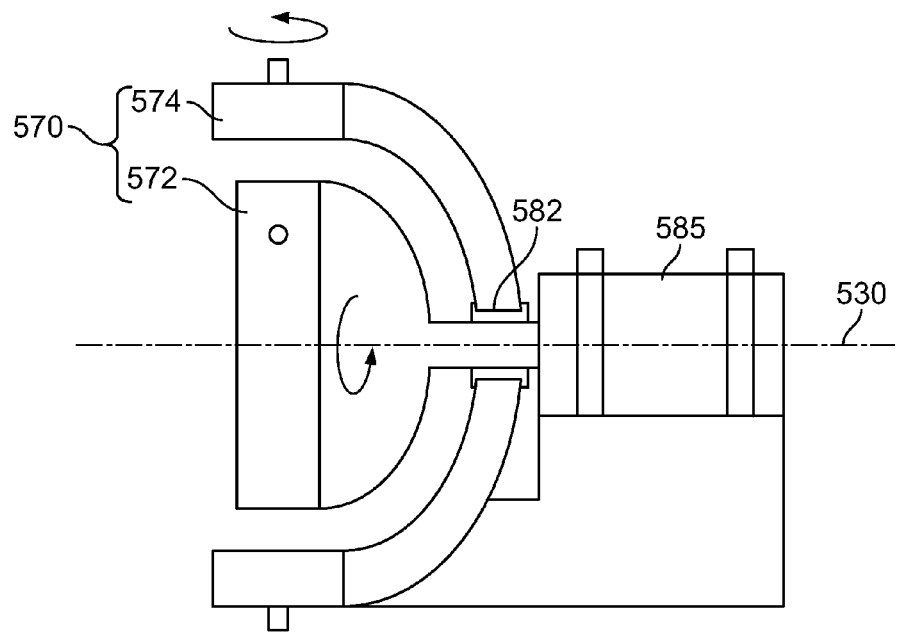
FIG. 5D is a side view of the motor driven collimator assembly of FIG. 1C.

Referring now to FIGS. 5A and 5B, housing 505 comprises an X-ray tube 540 (shown separated out from housing 505 in FIG. 5B) whose anode 541, also referred to as a target, emits a spatially localized X-ray beam 545a through an opening 542, also referred to as an aperture. A shield 543, formed of an X-ray absorptive material, such as tungsten, steel, lead or uranium, is disposed to surround and enclose anode 541 to absorb stray radiation emitted from anode 541. Further, the anode is surrounded by a highly absorbing block or material 593 (typically tungsten, steel and/or lead) through which opening 542 is defined. In an embodiment, opening 542 is a cone beam collimator slot and defines the overall area for X-ray emission, emitted from anode 541 in the form of beam 545a, with the moving collimator parts described below. In some embodiments, opening 542 is shaped so that X-ray beam 545a emanates as a cone beam. Also, in an embodiment, the head portion of X-ray tube 540, comprising opening 542, is shaped in a substantially spherical form. A cathode and heater filament assembly (not shown) may be configured, similar to embodiments described in above relation to the pencil beam embodiment.

An embodiment of collimator assembly 570 comprises a collimator 572, also referred to as a limiting element, partially surrounded by a shaped support or cradle element 574. In various embodiments, support or cradle 574 has a substantially semi-circular, 'U' or 'C' shape. In an embodiment, collimator 572 is a circular disk having a first radius. In one embodiment, where cradle 574 is substantially semi-circular shaped, it has a second radius, greater than the first radius, so that cradle 574 partially encompasses collimator 572. In accordance with an embodiment collimator 572 and cradle 574 are positioned between openings 543 and 544 such that a movement of collimator assembly 570 defines, shapes or forms X-ray beam 545a into pencil shaped X-ray beam 545b.

Referring now to FIGS. 5A through 5E, in one embodiment, the respective centers of collimator 572 and cradle 574 are substantially coaxial with central longitudinal axis 530 of housing 505. Collimator 572 has a transmission pattern in the form of a through opening 573 at a point between the center and the circumference of element 572. Collimator 572 is rotatable, about central longitudinal axis 530, through a bearing 582 supported by shaped cradle 574. Cradle 574 is fixed to pivoting mounts that allow cradle 572 to be oscillated about a vertical axis 532. In accordance with an aspect of the present specification, a motor 585 rotates or spins collimator 572, at a speed, about central longitudinal axis 530 while the supporting element or cradle 574 vibrates or oscillates, from side to side, about vertical axis 532 thereby causing the rotating or spinning collimator 572 to also vibrate or oscillate. In various embodiments, collimator 572 rotates at a speed ranging between 100 to 5000 RPM. In one embodiment, collimator 572 speed is 2000 RPM.

Figure 5E:
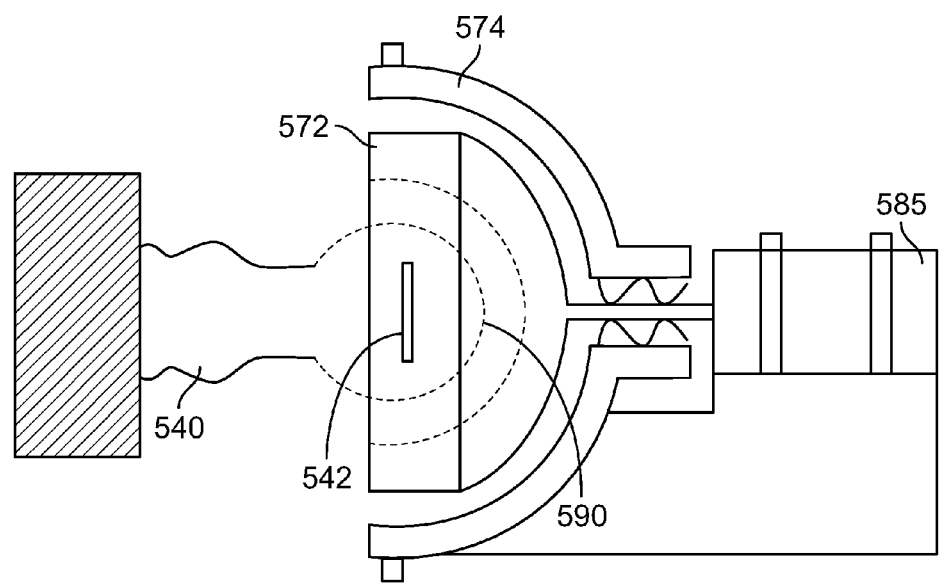
FIG. 5E is a substantially spherical head portion of an X-ray tube positioned within the collimator assembly, in accordance with an embodiment.

Rotating collimator 572 defines pencil beam 545b that sweeps a trajectory in a substantially vertical plane where the X-ray focal spot is in the plane of collimator 572 and on longitudinal axis 530 of bearing 582. The vibratory or oscillatory movement of cradle 574 and therefore that of collimator 572 causes pencil beam 545b to sweep over the substantially vertical plane moving from left to right and back again. The combined effect of the rotatory or spinning and oscillatory or vibratory movement of the collimator assembly 570 is one where pencil beam 545b moves in a raster pattern over a two dimensional area of the object under inspection. FIG. 5E shows X-ray tube 540 positioned within the moving collimator assembly 570 so that the substantially spherical shaped head portion 590 of X-ray tube 540, comprising opening 542, and rotating collimator 572 (supported by cradle 574) enable tight radiation collimation as X-ray beam 545b is scanned. The substantially spherical shaped head portion 590 of X-ray tube 540 allows the rotating and rocking or oscillating collimator 572 to efficiently move around head 590 with minimum radiation leakage.

A plurality of X-ray backscatter detectors 550 are configured and operated similar to detectors 150 already described in context of FIGS. 1A and 1B. Similarly, energy of the X-rays and signal quality can be maintained in a manner described earlier in context of the pencil beam embodiments.

In one embodiment, detectors 550 are scintillator based detector arrays with light guide readout to photomultiplier tubes.

Figure 5F:
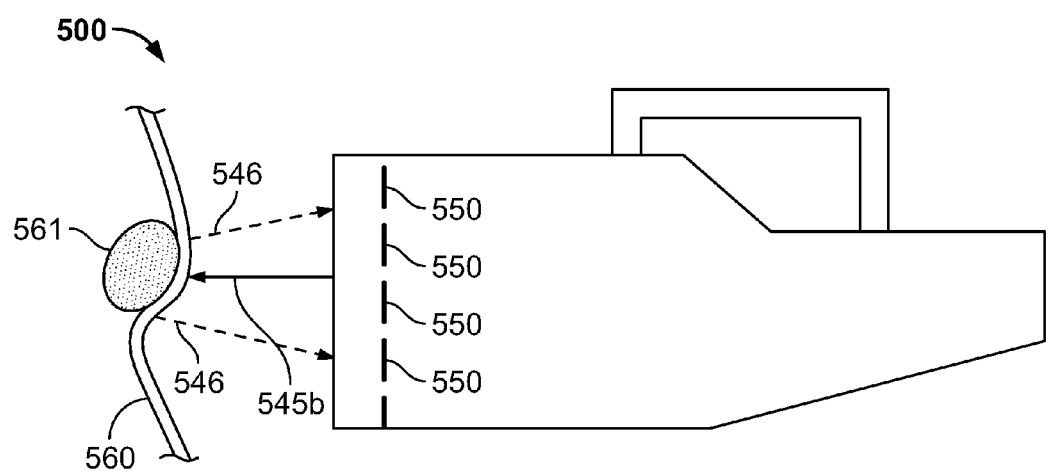
FIG. 5F illustrates the hand-held portable scanning device of the present specification projecting an X-ray beam over an object under inspection, in an embodiment.

During operation, as shown in FIG. 5F, shaped X-ray beam 545b interacts with an object 560 under inspection to produce scattered X-rays 546. As shown, object 560 conceals therein, an item or material 561. Scattered X-rays 546 are then detected by detectors 550 to produce scan data signal whose intensity is related to the effective atomic number (Z) near to the surface of object 560. Any one or a combination of the collimation systems disclosed above may be combined with this embodiment.

Figure 6A:
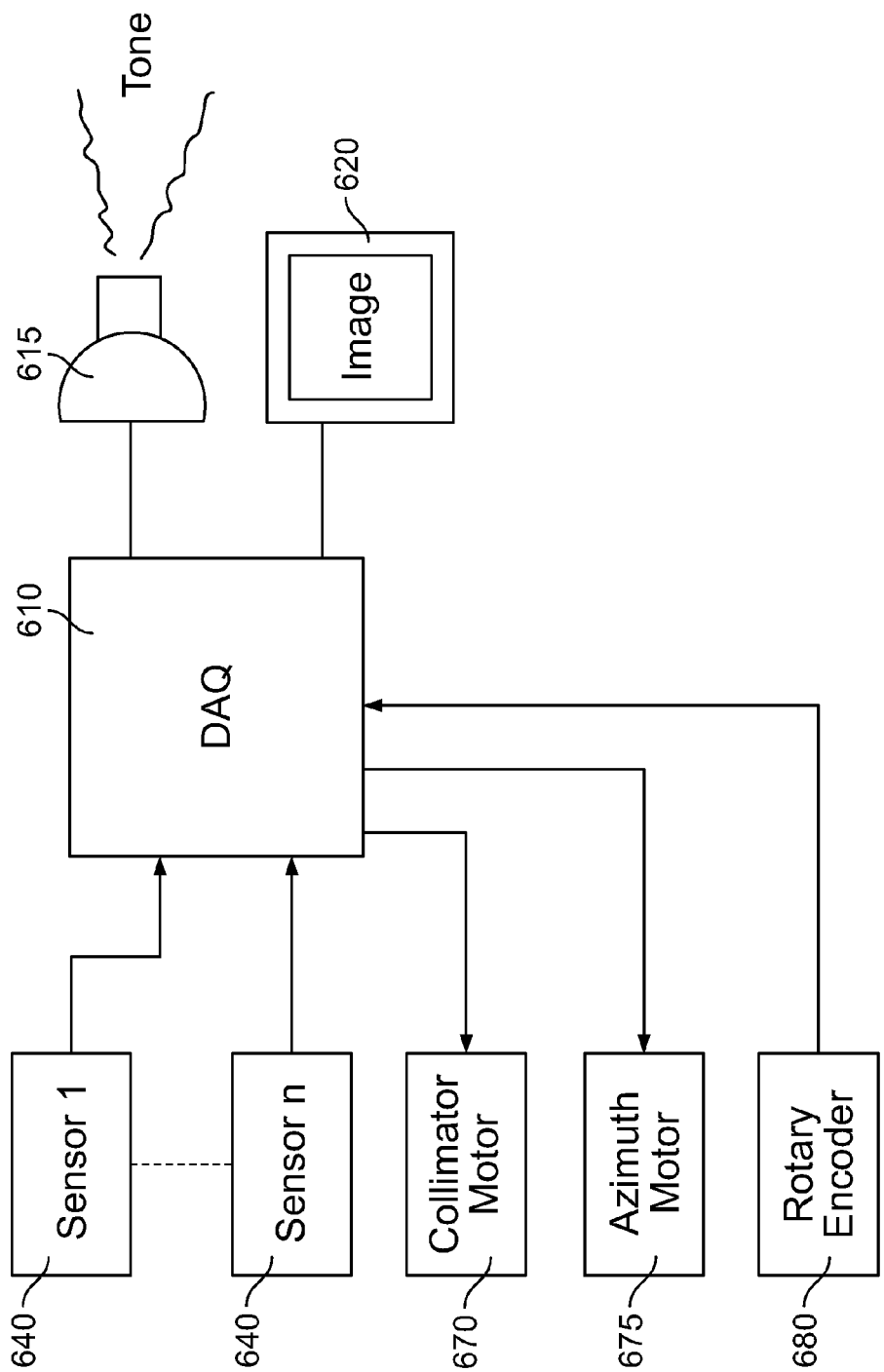
FIG. 6A is a block diagram illustrating a data acquisition system and a processing element in data communication with a plurality of detectors, a collimator motor, an azimuth motor, and a rotary encoder, in an embodiment of the present specification.

The position of the collimators is used to accurately correct images. Referring to FIG. 6A, a plurality of sensors 640 (corresponding to at least one of the detectors or detector systems mentioned in the embodiments above) is used to acquire data and communicate that data to a data acquisition system (DAQ) 610. DAQ 610, in turn, controls motor drivers responsible for creating collimator motion. Such motors include an azimuth motor 675 and a collimator motor 670. Rotary encoders 680 monitor the absolute position of the collimators and supply that information to DAQ 610 which, in turn, uses it to correct an acquired image based upon such position data.

Figure 6B:
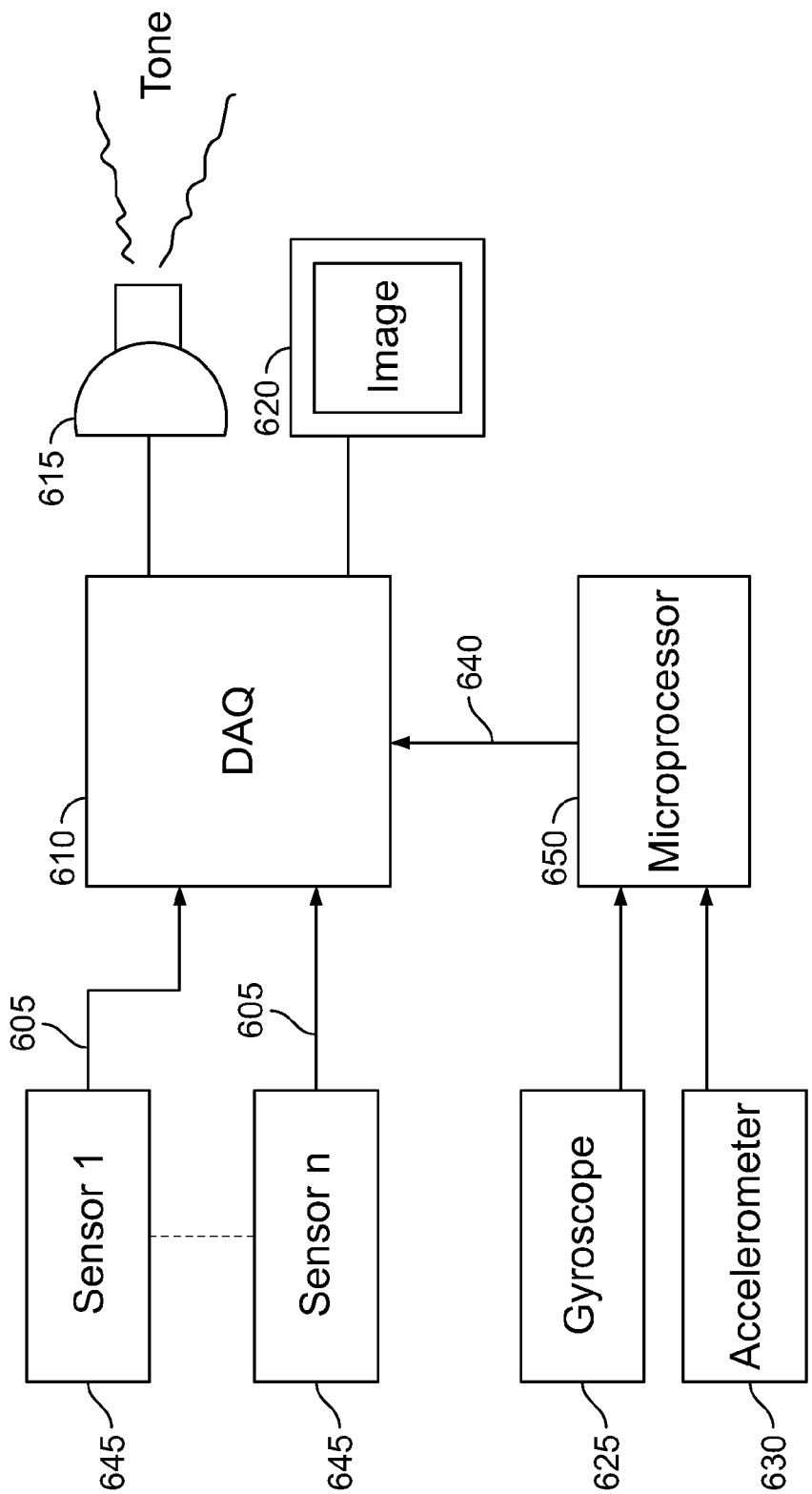
FIG. 6B is a block diagram illustrating a data acquisition system and a processing element in data communication with a plurality of detectors, a gyroscope and an accelerometer, in an embodiment of the present specification; and, FIG. 7 is a flow chart illustrating exemplary steps of a method of scanning an object using the hand-held portable device of the present specification.

As shown in FIG. 6B, in another embodiment, scan data 605 produced by plurality of detectors 645 (corresponding to at least one of the detectors or detector systems mentioned in the embodiments above) is accumulated into DAQ 610 wherein scan data 605 is summed within appropriate or optimal sampling time slots, time bins, or time periods. It should be appreciated that the shorter the sampling time period the noisier is the collected scan data but the more accurate or focused it is in terms of spatial location. In various embodiments scan data 605 sampling time slots, time bins, or time periods vary between 0.01 ms and 100 ms. In one embodiment, scan data 605 sampling time slot or time period is of 1 ms duration. A processing element 650, such as a microprocessor or a digital signal processor (DSP), is in data communication with DAQ 610 to perform a plurality of analyses or calculations using at least scan data 605. In one embodiment, scan data 605 is analyzed by comparing a mean scan signal level calculated over one or more temporal sampling periods with a background reference level. The bigger the difference between the sampled signal and the background level, the more substantial is the scattering object.

In accordance with an embodiment where a fan beam is utilized, the analysis is computed behind each of the plurality of collimator vanes 255 (FIGS. 2A, 2B), independently, in order to enable spatial localization and detection of even small anomalies. In further embodiments, to improve signal-to-noise ratio, the intensity of detected scatter signal 605 is estimated over all detectors 645 (corresponding to at least one of the detectors or detector systems mentioned in the embodiments above) by calculating a weighted sum of the pixel based and total signal data analysis.

In accordance with an aspect of the present specification, for each of the embodiments (illustrated in FIGS. 6A and 6B) disclosed above, the detected scatter scan data 605 is utilized to generate an alarm or feedback for the operator. In various embodiments the alarm or feedback is in the form of an audible tone and/or a scan image of the object under inspection. Accordingly, detected scatter scan data 605 is converted, using a speaker 615, into an audible tone or alarm, the pitch or frequency of which, in one embodiment, is directly proportional to the scatter signal. For example, speaker 615 emits a background tone at about 100 Hz with an average signal of 1000 detected scatter X-rays producing a frequency of about 400 Hz. Thus, a scattering object which generates a signal of 500 detected scatter X-rays would produce a tone at about 250 Hz. It will be appreciated by one of ordinary skill in the art that alternative mapping between detected scatter signal and audible tone or alarm can be envisioned, such as one which provides an exponential increase in tone, pitch or frequency to provide greater contrast for low scattering objects than for high scattering ones.

The probability of an X-ray photon interacting with the object under inspection depends strongly on the atomic number of the object—that is, the higher the atomic number the higher the probability of interaction. Similarly, the probability of absorbing a Compton scattered X-ray also depends strongly on the atomic number of the object under inspection. Therefore, it is known by those skilled in the art that the Compton backscatter signal is highest for low atomic number materials such as organic materials and people and is smallest for high atomic number materials such as steel and lead.

Additionally or alternatively, the scan image of the object under inspection is displayed on at least one display 620. A visual feedback, such as the scan image, is advantageous to enable the operator to notice subtle differences between one scattering object and another since the human visual system has a natural ability at identifying shapes and associating these shapes with specific threats (such as a gun or a knife). Referring to FIG. 6B, in order to form the scan image, an embodiment of the present specification includes a 3D gyroscope 625 and/or a 3D accelerometer 630 within the respective housings. 3D gyroscope 625 is used to track a first data stream indicative of an absolute position or pointing direction of the X-ray beam or hand-held device in 3D space, while 3D accelerometer 630 tracks a second data stream indicative of rapid relative movements of the X-ray beam in 3D space. In accordance with an embodiment, the first and second data streams are input into and combined by processing element 650 to generate position or coordinates 640 of the X-ray beam at all times during scanning operation, even in response to rapid movement of the beam or hand-held device (in embodiments described above) by the operator.

According to an aspect of the present specification, each position or coordinate of the X-ray beam in 3D space has associated plurality of active pixels that correspond to the particular spatial location, on the object under inspection, where the X-ray beam is interacting. These active pixels are located within a matrix of other potentially active pixels which together constitute an image. In a practical scenario, it is reasonable to assume that the operator will sweep the X-ray beam over the object more than once causing multiple scan frames to contribute to a pixel in the image. Therefore, in order to ensure a quantitative image, the brightness or scan data of each pixel is corrected by the total X-ray beam dwell time at that pixel location. This dwell time is calculated over all periods that the X-ray beam is present over each active pixel.

The number of X-rays reaching the object under inspection is defined by the X-ray beam collimator aperture and beam divergence. The area of the object under inspection that is covered by the X-ray beam is then determined by the distance of the X-ray source from the object under inspection—that is, the larger the distance the larger the area of the object covered by the X-ray beam. The number of scattered X-rays that return to the detector is inversely proportional to the distance between the object under inspection and the detector array. Thus, in one operating condition, the hand-held device of the present specification as described in various embodiments above is held close to the object under inspection, so that the area of the object irradiated by the X-ray beam is small and the fraction of the scattered signal collected by the detector is high.

Figure 7:
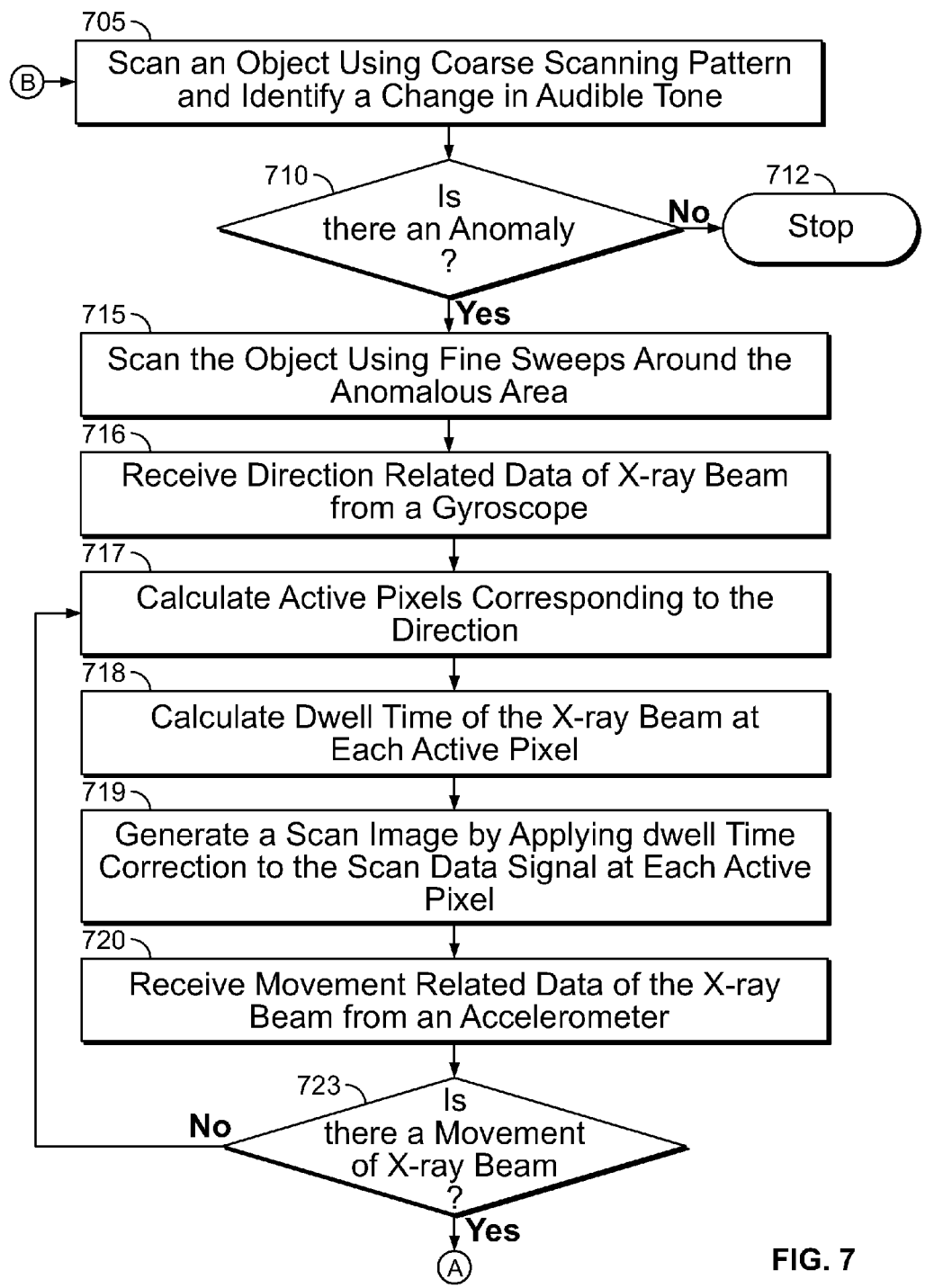
Figure 7:
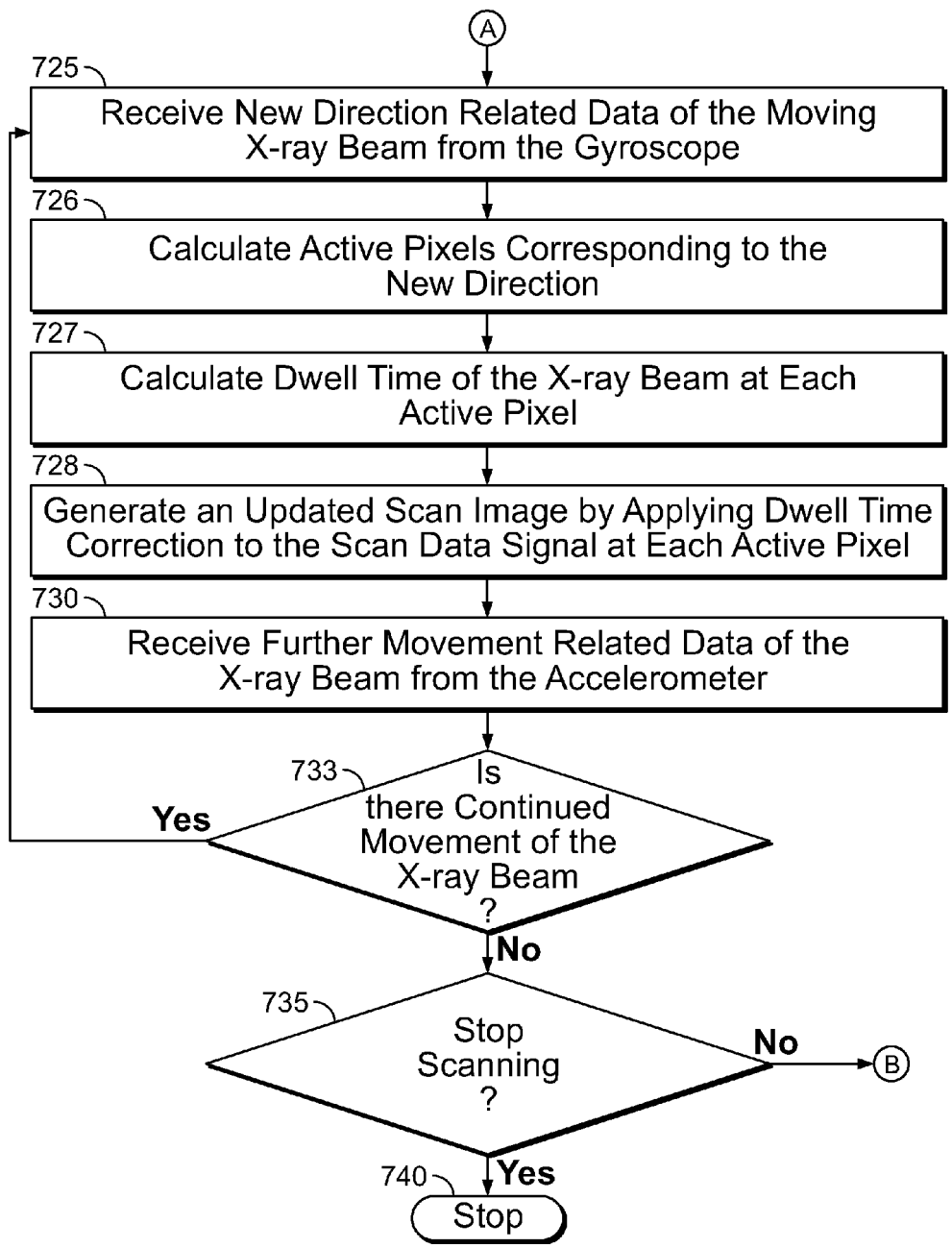

FIG. 7 is a flow chart illustrating a plurality of exemplary steps of a method of scanning an object using an X-ray beam projected by the hand-held portable device of the present specification. At 705, an operator first sweeps the X-ray beam onto the object using a coarse scanning pattern during which a change in audible tone is used as the primary feedback to identify anomalies with reference to the object. The coarse scanning pattern, in one embodiment, refers to a fairly quick scanning or sweeping movement of the X-ray beam over the surface of the object, referred to as the general scanning area, where the coarse scanning pattern is defined as having a first density of X-ray coverage over the general scanning area. If no anomaly is identified, at 710, then the scan of the object is stopped, at 712, and a new scan session for another object can begin, if required. However, if an anomaly is identified, at 710, the operator then proceeds to make fine scanning patterns or relatively slower movements of the X-ray beam around the anomalous area, at 715, where the fine scanning pattern is defined as having a second density of X-ray coverage over the anomalous area. It should be appreciated that the anomalous area is smaller than, but positioned within, the general scanning area. It should also be appreciated that the second density (associated with the fine scanning pattern) is greater than the first density (associated with the coarse scanning pattern).

On initiating the fine sweep scanning of the object, the followings tasks are performed: at 716, data is received from a 3D gyroscope representing a direction of pointing of the X-ray beam projected onto the object; at 717 a plurality of active pixels corresponding to the direction of the X-ray beam are calculated; at 718, a dwell time of the X-ray beam at each of the active pixels is calculated; and at 719, a scan image after correcting the scan data signal is generated, at each of the active pixels, using the dwell time. At 720, data from a 3D accelerometer is obtained to check if there is a movement of the X-ray beam relative to the direction of the X-ray beam obtained at 716. If there is no movement of the X-ray beam detected, at 723, then the steps 717 to 720 are repeated (till a movement of the X-ray beam is detected).

However, if a movement of the X-ray beam is detected, at 723, then the following tasks are performed: at 725, data is received from the 3D gyroscope representing a new direction of the X-ray beam due to the movement of the X-ray beam; at 726, a plurality of active new pixels corresponding to the new direction of the X-ray beam are calculated; at 727, a dwell time of the X-ray beam at each of the active new pixels is calculated; and at 728, an updated scan image is generated after applying the dwell time correction to the scan data signal at each active pixel.

At 730, data from the 3D accelerometer is obtained again to check if there is a continued movement of the X-ray beam. If it is determined at 733 that the X-ray beam is still moving or being swept over the object, then steps 725 to 730 are repeated (till the X-ray beam sweeping movement stops). However, in case there is no detected movement of the projected X-ray beam at 733, then at 735 a check is performed to determine whether the scanning has to be stopped (and therefore, move to 740) or another scanning session or event should begin from 705 onwards. The scan image generated at 719 and/or 728 is visually analyzed by the operator to determine further features of the anomaly and declare the anomaly as benign or threat.

In various embodiments of the present specification, the hand-held device of the present specification, such as those in embodiments described above, includes a laser-beam range finder or any other suitable optical sensor beam, known to persons of ordinary skill in the art, is used to propagate an optical, visible light or laser beam along the central path of the X-ray beam (for example, by deflecting a laser beam using a thin gold coated Mylar film reflector in the X-ray beam path). The directed optical or laser beam is used to calculate the distance of the hand-held device from the object under inspection so that the surface of the object can be reconstructed in three-dimensional (3D) space (using the measured distance to the surface of the object taken in combination with the gyroscope and/or accelerometer data) in order to create an X-ray image that wraps around the three-dimensional surface of the object under inspection. Such a three-dimensional view can help the image interpreter or operator to better identify or estimate the exact location of the anomaly or threat object, area or region.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method of scanning an object by projecting a shaped X-ray beam from a hand-held imaging device, said device comprising a housing enclosing an X-ray tube that emits the shaped X-ray beam, a plurality of detectors for generating scan data embodied in an image comprising pixels and corresponding to a plurality of detected X-ray beams scattered from the object, a processor in communication with a gyroscope and an accelerometer, and an acquisition system in communication with a speaker, a display, said processor and said plurality of detectors, the method comprising:

receiving, at the processor, data generated from the gyroscope and data generated from the accelerometer, wherein the data generated from the gyroscope and the data generated by the accelerometer are indicative of a movement of the shaped X-ray beam being projected on the object;

generating, using the processor, data corresponding to a location of interaction of the shaped X-ray beam on the object based on the data generated from the gyroscope and data generated from the accelerometer;

determining, using the processor, a plurality of active pixels of said pixels that correspond to the location of interaction of the shaped X-ray beam on the object;

calculating a time duration, using the processor, at each of said plurality of active pixels, for which the shaped X-ray beam is present over each of said plurality of active pixels; and generating, using the processor, an image, on said display, of the object after correcting the scan data, at each of said plurality of active pixels, using said time duration.

2. The method of claim 1, wherein said shaped X-ray beam is in the form of at least one of a pencil beam, a fan beam, a cone beam, a single axis rotating beam, and a double axis rotating beam.

3. The method of claim 1, wherein the hand-held imaging device is swept to scan the object using a coarse scanning pattern to identify at least one anomaly, with reference to the object, prior to determining said plurality of active pixels, calculating said time duration and generating said image.

4. The method of claim 3, wherein said at least one anomaly is identified based on a change in audible tone generated by the speaker.

5. The method of claim 4, wherein the processor and speaker are adapted to generate said audible tone such that a pitch or frequency of said audible tone varies in proportion to said scan data.

6. The method of claim 3, wherein upon identification of said at least one anomaly, the hand-held imaging device is swept to scan the object using a fine scanning pattern for determining said plurality of active pixels, calculating said time duration and generating said image.

7. The method of claim 1, further comprising receiving new data generated by the accelerometer, wherein the new data generated by the accelerometer is indicative of a movement of the shaped X-ray beam being projected on the object and wherein based on the new data generated by the accelerometer:

determining, using the processor, a new plurality of active pixels corresponding to a new location of interaction of the shaped X-ray beam on the object;

calculating, using the processor, a new time duration, at each of said new plurality of active pixels, for which the shaped X-ray beam is present over each of the new plurality of active pixels; and generating using the processor, an updated image, on said display, of the object after correcting the scan data, at each of said new plurality of active pixels, using the new time duration.

8. The method of claim 7, wherein said new location is associated with new data generated by the gyroscope, and wherein the new data generated by the gyroscope is indicative of a new direction of the shaped X-ray beam being projected on the object.

9. The method of claim 1, wherein the acquisition system sums said detected scan data over a sampling duration ranging between 0.01 ms and 100 ms.

10. The method of claim 1, wherein the acquisition system sums said detected scan data over a sampling duration of 1 ms.

11. The method of claim 1, wherein a voltage of the X-ray tube ranges between 30 kV and 100 kV.

12. The method of claim 1, wherein a current of the X-ray tube ranges between 0.1 mA and 5 mA.

13. A hand-held imaging device for scanning an object by projecting a shaped X-ray beam, the device comprising:

a housing having a central longitudinal axis and comprising:

a plurality of detectors for generating scan data corresponding to an image and comprising pixels corresponding to a plurality of detected X-ray beams scattered from the object;

a gyroscope configured to generate first data indicative of a movement of the shaped X-ray beam being projected on the object;

an accelerometer configured to generate second data indicative of a movement of the shaped X-ray beam being projected on the object;

an acquisition system in communication with a display and said plurality of detectors; and a processor in communication with said gyroscope, said accelerometer and said acquisition system, wherein said processor is configured to:
  determine a location of interaction of the shaped X-ray beam on the object based on the first data and the second data;
  determine a plurality of active pixels of the pixels corresponding to the location of interaction of the shaped X-ray beam on the object;
  calculating a time duration, at each of said plurality of active pixels, for which the shaped X-ray beam is present over each of said plurality of active pixels; and
  generating an image, on said display, of the object after correcting the scan data, at each of said plurality of active pixels, using said time duration.

14. The device of claim 13, wherein said shaped X-ray beam is in the form of at least one of a pencil beam, a fan beam, a cone beam, a single axis rotating beam, and a double axis rotating beam.

15. The device of claim 13, wherein said housing has an upper surface, a base opposite and parallel to said upper surface, a front surface, a rear surface opposite and parallel to said front surface, a first side and a second side opposite and parallel to said first side, and wherein said upper surface has at least one handle.

16. The device of claim 15, wherein said housing is configured as a first cuboid, bearing said front surface, which tapers along the central longitudinal axis into a trapezoidal prism culminating in said rear surface.

17. The device of claim 15, wherein said shaped X-ray beam emerges through an opening at a center of said front surface in a direction substantially perpendicular to said front surface.

18. The device of claim 17, wherein said plurality of detectors are positioned adjacent to and behind said front surface surrounding said opening at the center of said front surface.

19. The device of claim 13, further comprising a speaker, wherein said processor and speaker are adapted to generate an audible tone such that a pitch or frequency of said audible tone varies in proportion to said scan data.

* * * * *